United States Patent

Harnett et al.

(10) Patent No.: US 6,936,715 B2
(45) Date of Patent: Aug. 30, 2005

(54) LIPOIC ACID HETEROCYCLIC OR BENZENE DERIVATIVES, PREPARATION AND USE THEREOF AS MEDICINES

(75) Inventors: Jeremiah Harnett, Gif-Sur-Yvette (FR); Michel Auguet, Palaiseau (FR)

(73) Assignee: Societe de Conseils de Recherches et d'Applications Scientifiques (FR)

( * ) Notice: Subject to any disclaimer, the term of this patent is extended or adjusted under 35 U.S.C. 154(b) by 63 days.

(21) Appl. No.: 10/221,432

(22) PCT Filed: Mar. 15, 2001

(86) PCT No.: PCT/FR01/00764

§ 371 (c)(1),
(2), (4) Date: Sep. 10, 2002

(87) PCT Pub. No.: WO01/68643

PCT Pub. Date: Sep. 20, 2001

(65) Prior Publication Data

US 2003/0105107 A1 Jun. 5, 2003

(30) Foreign Application Priority Data

Mar. 16, 2000 (FR) .............................................. 00 03355
Sep. 21, 2000 (FR) .............................................. 00 12007

(51) Int. Cl.$^7$ .......................................... C07D 409/14
(52) U.S. Cl. ....................... 544/369; 544/372; 544/374; 544/379; 546/332; 549/35; 564/225
(58) Field of Search ................................ 544/369, 372, 544/374, 379; 546/332; 549/35; 564/225

(56) References Cited

U.S. PATENT DOCUMENTS 5,364,871 A * 11/1994 Takasugi et al. ............ 514/342

6,030,985 A 2/2000 Gentile et al. .............. 514/307

FOREIGN PATENT DOCUMENTS

| EP | 0798292 | 10/1997 |
| EP | 0869126 | 10/1998 |
| FR | 2761066 | 9/1998 |
| FR | 2801053 | 5/2001 |
| WO | 0059899 | 10/2002 |

OTHER PUBLICATIONS

Jackson, M. et al, Expert. Opin. Investig. Drugs, 11(10) 2002, 1343–1364.*

* cited by examiner

Primary Examiner—Thomas C. McKenzie
(74) Attorney, Agent, or Firm—Charles A. Muserlian

(57) ABSTRACT

Compounds of the formulae

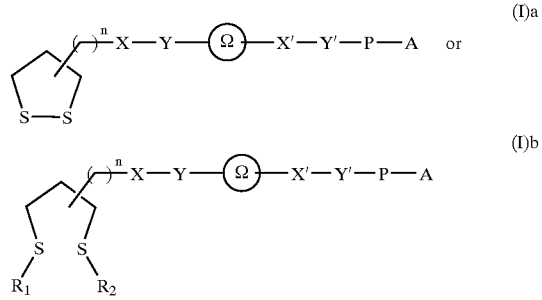

wherein the substituents are as defined in the specification useful for inhibiting NO synthase and regenerate antioxidants.

6 Claims, No Drawings

LIPOIC ACID HETEROCYCLIC OR BENZENE DERIVATIVES, PREPARATION AND USE THEREOF AS MEDICINES

This application is a 371 of PCT/FR01/00764 filed Mar. 15, 2001.

A subject of the present invention is new heterocyclic or benzenic derivatives comprising a lateral chain derived from lipoic acid, which have an inhibitory activity on NO-synthase enzymes producing nitrogen monoxide NO and/or are agents which allow the regeneration of antioxidants or entities which trap the reactive oxygen species (ROS) and which intervene in a more general fashion in the redox status of thiol groups. These antioxidants or entities which trap the reactive oxygen species can be of natural origin, such as for example vitamin E or glutathione, or of synthetic origin such as certain products which trap the ROS or products having both an inhibitory activity on NO-synthase enzymes and an activity which traps the ROS. Examples of such products of synthetic origin can in particular be found in the PCT Patent Applications WO 96/09653, WO 98/42696 and WO 98/58934.

Therefore, the invention relates in particular to the derivatives corresponding to general formula (I) defined below, their preparation processes, the pharmaceutical preparations containing them and their use for therapeutic purposes, in particular their use as NO-synthase inhibitors and/or as agents which allow the regeneration of antioxidants or entities which trap the ROS's and which intervene in a more general fashion in the redox status of thiol groups.

Given the potential role of NO and the ROS's and the metabolism of glutathione in physiopathology, the new derivatives described corresponding to general formula (I) may produce beneficial or favourable effects in the treatment of pathologies where nitrogen monoxide and the metabolism of glutathione as well as the redox status of thiol groups are involved. In particular:

- cardiovascular and cerebrovascular disorders including for example atherosclerosis, migraine, arterial hypertension, septic shock, ischemic or hemorragic cardiac or cerebral infarctions, ischemias and thromboses.
- disorders of the central or peripheral nervous system such as for example neurodegenerative diseases where there can in particular be mentioned cerebral infarctions, sub-arachnoid haemorrhaging, ageing, senile dementias including Alzheimer's disease, Huntington's chorea, Parkinson's disease, Creutzfeld Jacob disease and prion diseases, amyotrophic lateral sclerosis but also pain, cerebral and spinal cord traumas, addiction to opiates, alcohol and addictive substances, erective and reproductive disorders, cognitive disorders, encephalopathies, encephalopathies of viral or toxic origin, depression, anxiety, schizophrenia, epilepsy, sleeping disorders, eating disorders (anorexia, bulimia etc.);
- disorders of the skeletal muscle and neuromuscular joints (myopathy, myositis) as well as cutaneous diseases.
- proliferative and inflammatory diseases such as for example atherosclerosis, pulmonary hypertension, respiratory distress, glomerulonephritis, cataracts, portal hypertension, psoriasis, arthrosis and rheumatoid arthritis, fibroses, amyloidoses, inflammations of the gastro-intestinal system (colitis, Crohn's disease) or of the pulmonary system and airways (asthma, sinusitis, rhinitis) as well as contact or delayed hypersensitivities;
- organ transplants.
- auto-immune and viral diseases such as for example lupus, AIDS, parasitic and viral infections, diabetes and its complications including retinopathies, nephropathies and polyneuropathies, multiple sclerosis, myopathies;
- cancer.
- autosomal genetic diseases such as Unverricht-Lundborg disease;
- neurological diseases associated with intoxications (Cadmium poisoning, inhalation of n-hexane, pesticides, herbicides), associated with treatments (radiotherapy) or disorders of genetic origin (Wilson's disease).
- impotence linked to diabetes;
- all the pathologies characterized by an excessive production or a dysfunction of nitrogen monoxide and/or the metabolism of glutathione and of the redox status of the thiol groups.

In all these pathologies, there is experimental evidence demonstrating the involvement of nitrogen monoxide or of a dysfunction of the metabolism of glutathione (Kerwin et al., Nitric oxide: a new paradigm for second messengers, *J. Med. Chem.* 38, 4343–4362, 1995; Packer et al., Alpha-lipoic acid as biological antioxidant, *Free Radical Biology & Medicine* 19, 227–250, 1995). This is the case in particular in Parkinson's disease (Beal M F, Excitotoxicity and nitric oxide in Parkinson's disease pathogenesis. *Ann. Neurol.* 44[Suppl 1], S110–114, 1998; Donato et al., Gluthathion in Parkinson's disease: a link between oxidative stress and mitochondrial damage. *Ann. Neurol.* 32, S111–115, 1992). In this context, medicaments which can inhibit the formation of nitrogen monoxide or re-establish the biological functionality of the thiol groups or glutathione can have beneficial effects.

Moreover, in earlier patents, the inventors have already described NO Synthase inhibitors and their use (U.S. Pat. Nos. 5,081,148; 5,360,925) and more recently the combination of these inhibitors with products having antioxidant or antiradicular properties (PCT Patent Application WO 98/09653). They have also described derivatives of amidines in PCT Patent Applications WO 98/42696 and WO 98/58934 and the derivatives of aminopyridines in the PCT Patent Application WO 00/02860. These derivatives of amidines or aminopyridines have the characteristic of being both NO Synthase inhibitors and ROS inhibitors A subject of the present invention is new heterocyclic or benzenic derivatives comprising a lateral chain derived from lipoic acid, their preparation and their therapeutic use.

The invention relates therefore to a product of general formula (I), characterized in that it comprises the products of sub-formulae (I)a and (I)b

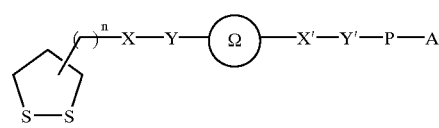

(I)a

-continued

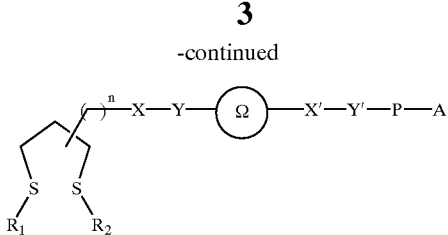
(I)b in which n represents an integer from 0 to 6;

$R_1$ and $R_2$ represent, independently, a hydrogen atom or a linear or branched alkyl radical with 1 to 6 carbon atoms;

X—Y represents —O—$(CH_2)_r$—, —$N(R_3)$—$(CH_2)_r$—, —$CO(CH_2)_r$—, —CO—$N(R_3)$—$(CH_2)_r$—, —$N(R_4)$—CO—$(CH_2)_r$—, or —$N(R_3)$—CO—$N(R_4)$—$(CH_2)_r$—, X'—Y' represents —$(CH_2)_r$—, —$(CH_2)_r$—O—$(CH_2)_r$—, —$(CH_2)_r$—$N(R_3)$—$(CH_2)_r$—, —$(CH_2)_r$—$CO(CH_2)_r$—, —$(CH_2)_r$—CO—$N(R_3)$—$(CH_2)_r$—, —$(CH_2)_r$—$N(R_4)$—CO—$(CH_2)_r$—, or —$(CH_2)_r$—$N(R_3)$—CO—$N(R_4)$—$(CH_2)_r$—, $R_3$ and $R_4$ represent, independently each time that they occur, a hydrogen atom or an alkyl, alkoxycarbonyl or aralkoxycarbonyl radical;

r representing independently each time that it occurs an integer from 0 to 6;

Ω represents an aromatic heterocycle with 5 or 6 members, a non aromatic heterocycle with 4 to 7 members or a phenylene radical substituted by an $R_5$ radical, $R_5$ representing a hydrogen atom, a linear or branched alkyl radical with 1 to 6 carbon atoms or a —$(CH_2)_m$—Q radical in which Q represents a halogen atom or a hydroxy, cyano, amino, alkoxy, alkylamino or dialkylamino radical, m representing an integer from 0 to 6;

P represents —$(CH_2)_g$—, g representing an integer from 0 to 6, or also P represents an

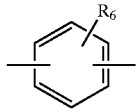

radical in which $R_6$ represents a hydrogen atom, a linear or branched alkyl radical with 1 to 6 carbon atoms or a —$(CH_2)_n$—Q' radical in which Q' represents a halogen atom or a trifluoromethyl, hydroxy, amino, cyano, alkoxycarbonylamino, aralkoxycarbonylamino, alkoxy, alkylthio, alkylamino or dialkylamino radical and n represents an integer from 0 to 6, or also $R_6$ represents an aromatic or non aromatic heterocycle with 5 to 6 members the heterocyclic members of which are chosen from the —O—, —$N(R_7)$— and —S— radicals, $R_7$ representing a hydrogen atom or a linear or branched alkyl with 1 to 6 carbon atoms;

and finally A represents the

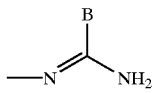

radical in which:

B represents a linear or branched alkyl radical with 1 to 6 carbon atoms, carbocyclic or heterocyclic aryl radical with 5 or 6 members containing from 1 to 4 heteroatoms chosen from O, S and N and in particular the thiophene, furan, pyrrole or thiazole radicals, the aryl radical being optionally substituted by one or more groups chosen from the linear or branched alkyl, alkenyl or alkoxy radicals with 1 to 6 carbon atoms, or B represents $NR_8R_9$, in which $R_8$ and $R_9$ represent, independently, a hydrogen atom or a linear or branched alkyl radical with 1 to 6 carbon atoms, or one of $R_8$ and $R_9$ represents a nitro radical whilst the other represents a hydrogen atom or a linear or branched alkyl radical with 1 to 6 carbon atoms, or also $R_8$ and $R_9$ when taken together form with the nitrogen atom a non aromatic heterocycle with five to six members, the elements of the chain being chosen from a group comprising —$CH_2$—, —NH—, —O— or —S—, or also B represents an $SR_{10}$ radical in which $R_{10}$ represents a hydrogen atom or a linear or branched alkyl radical with 1 to 6 carbon atoms;

or a salt of a product of general formula (I).

By alkyl, unless otherwise specified, is meant a linear or branched alkyl radical containing 1 to 6 carbon atoms. By cycloalkyl, unless otherwise specified, is meant a monocyclic carbon system containing 3 to 7 carbon atoms. By alkenyl, unless otherwise specified, is meant a linear or branched alkyl radical containing 1 to 6 carbon atoms and with at least one unsaturation (double bond). By alkynyl, unless otherwise specified, is meant a linear or branched alkyl radical containing 1 to 6 carbon atoms and with at least one double unsaturation (triple bond). By allenyl, is meant the —CH═C═$CH_2$ radical. By carbocyclic or heterocyclic aryl, is meant a carbocyclic (in particular, the phenyl radical which can be abbreviated to Ph) or heterocyclic system comprising at least one aromatic ring, a system being called heterocyclic when at least one of the rings which comprises it contains a heteroatom (O, N or S). By heterocycle, unless otherwise specified, is meant a mono- or polycyclic system said system comprising at least one heteroatom chosen from O, N and S and being saturated, partially or totally unsaturated or aromatic. By heteroaryl, unless otherwise specified, is meant a heterocycle as defined previously in which at least one of the rings which comprise it is aromatic. By haloalkyl, is meant an alkyl radical at least one of the hydrogen atoms (and optionally all) of which is replaced by a halogen atom.

By alkylthio, alkoxy, haloalkyl, alkoxyalkyl, trifluoromethylalkyl, cycloalkylalkyl, haloalkoxy, aminoalkyl, alkenyl, alkynyl, allenylalkyl, cyanoalkyl and aralkyl radicals, is meant respectively the alkylthio, alkoxy, haloalkyl, alkoxyalkyl, trifluoromethylalkyl, cycloalkylalkyl, haloalkoxy, aminoalkyl, alkenyl, alkynyl, allenylalkyl, cyanoalkyl and aralkyl radicals the alkyl radical (the alkyl radicals) of which have the meaning(s) indicated previously.

By heterocycle, is meant in particular the thienyl, piperidyl, piperazinyl, quinolinyl, indolinyl and indolyl radicals. By linear or branched alkyl with 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. Finally, by halogen, is meant the fluorine, chlorine, bromine or iodine atoms.

Preferably, the invention relates to the compounds of general formula (I) in which at least one of the following characteristics is found:

n represents an integer from 1 to 6;

X—Y represents one of the —O—$(CH_2)_r$—, —$N(R_3)$—$(CH_2)_r$—, —$CO(CH_2)_r$—, —CO—$N(R_3)$—$(CH_2)_r$—, —$N(R_4)$—CO—$(CH_2)_r$—, or —$N(R_3)$—CO—N$(R_4)$—$(CH_2)_r$— radicals, in which $R_3$ and $R_4$ represent a hydrogen atom or an alkyl radical;

X'—Y' represents one of the —$(CH_2)_r$—, —$(CH_2)_r$—O—$(CH_2)_r$—, —$(CH_2)_r$—$N(R_3)$—$(CH_2)_r$—, —$(CH_2)_r$—

CO(CH$_2$)$_r$—, —(CH$_2$)$_r$—CO—N(R$_3$)—(CH$_2$)$_r$—, —(CH$_2$)$_r$—N(R$_4$)—CO—(CH$_2$)$_r$— or —(CH$_2$)$_r$—N(R$_3$)—CO—N(R$_4$)—(CH$_2$)$_r$— radicals, in which R$_3$ and R$_4$ represents a hydrogen atom or an alkyl or alkoxycarbonyl radical;

Ω represents a phenylene radical substituted by an R$_5$ radical, R$_5$ representing a hydrogen atom, a linear or branched alkyl radical with 1 to 6 carbon atoms or a —(CH$_2$)$_m$—Q radical in which Q represents a halogen atom or a cyano, amino or alkoxy, radical, m representing an integer from 0 to 6, or also Ω represents an aromatic heterocycle with 5 or 6 members or a non aromatic heterocycle with 4 to 7 members, said aromatic or non aromatic heterocycle preferably comprising at least one nitrogen atom;

P represents a

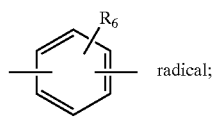 radical;

A represents a

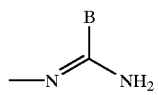

radical in which B represents a carbocyclic or heterocyclic aryl radical with 5 or 6 members containing from 1 to 4 heteroatoms chosen from O, S and N.

More preferentially, the invention relates to the compounds of general formula (I) in which at least one of the following characteristics is found:

n represents an integer from 1 to 5;
X—Y represents one of the —O—(CH$_2$)$_r$—, —N(R$_3$)—(CH$_2$)$_r$—, —CO(CH$_2$)$_r$—, —CO—N(R$_3$)—(CH$_2$)$_r$—, —N(R$_4$)—CO—(CH$_2$)$_r$—, or —N(R$_3$)—CO—N(R$_4$)—(CH$_2$)$_r$— radicals, in which R$_3$ and R$_4$ represents a hydrogen atom;
X'—Y' represents one of the —(CH$_2$)$_r$—, —(CH$_2$)$_r$—O—(CH$_2$)$_r$—, —(CH$_2$)$_r$—N(R$_3$)—(CH$_2$)$_r$—, —(CH$_2$)$_r$—CO(CH$_2$)$_r$—, —(CH$_2$)$_r$—CO—N(R$_3$)—(CH$_2$)$_r$—, —(CH$_2$)$_r$—N(R$_4$)—CO—(CH$_2$)$_r$— or —(CH$_2$)$_r$—N(R$_3$)—CO—N(R$_4$)—(CH$_2$)$_r$— radicals, in which R$_3$ and R$_4$ represent a hydrogen atom;
Ω represents a phenylene radical substituted by an R$_5$ radical, R$_5$ representing a hydrogen atom, a linear or branched alkyl radical with 1 to 6 carbon atoms or a —(CH$_2$)$_m$—Q radical in which Q represents a cyano, or alkoxy radical, or also Ω represents a non aromatic heterocycle with 4 to 7 members preferably comprising at least one nitrogen atom;
P represents a

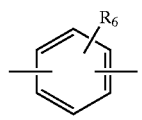

radical in which R$_6$ represents a —(CH$_2$)$_n$—Q' radical in which Q' represents a hydrogen atom or an alkoxy, cyano, amino, alkylamino or dialkylamino radical and n represents an integer from 0 to 6 and preferably an integer from 0 to 3;

A represents a

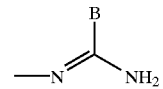

radical in which B represents a heterocyclic aryl radical with 5 or 6 members containing from 1 to 4 heteroatoms chosen from O, S and N.

Even more preferentially, the invention relates to the compounds of general formula (I) in which at least one of the following characteristics is found:

n represents an integer from 1 to 4;
X—Y represents one of the —CO(CH$_2$)$_r$—, —CO—N(R$_3$)—(CH$_2$)$_r$— or —N(R$_4$)—CO—(CH$_2$)$_r$— radicals, in which R$_3$ and R$_4$ represent a hydrogen atom;
X'—Y' represents one of the —(CH$_2$)$_r$— or —(CH$_2$)$_r$—N(R$_3$)—(CH$_2$)$_r$— or —(CH$_2$)$_r$—CO—N(R$_3$)—(CH$_2$)$_r$— radicals, in which R$_3$ and R$_4$ represent a hydrogen atom;
Ω represents a piperazinyl, piperidyl or phenyl radical, and preferably a piperazinyl or piperidyl radical;
P represents a

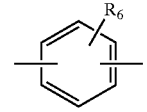

radical in which R$_6$ represents a —(CH$_2$)$_n$—Q' radical in which Q' represents a hydrogen atom or an alkoxy, cyano or amino radical and n represents an integer from 0 to 3;

A represents an

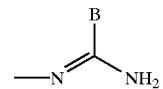

radical in which B represents a thienyl, furanyl or pyrrolyl radical.

Moreover, among the compounds of general formula (I) the compounds corresponding to sub-general formula (I)a are generally preferred.

More particularly, the invention relates to the following products described in the examples (sometimes in the form of salts):

N'-(4-{4-[5-(1,2-dithiolan-3-yl)pentanoyl]-1-piperazinyl}phenyl)-2-thiophenecarboximidamide;
N'-(4-{4-[2-(1,2-dithiolan-3-yl)acetyl]-1-piperazinyl}phenyl)-2-thiophenecarboximidamide;
N'-[3-({4-[5-(1,2-dithiolan-3-yl)pentanoyl]-1-piperazinyl}methyl)phenyl]-2-thiophenecarboximidamide;
N'-[3-({4-[2-(1,2-dithiolan-3-yl)acetyl]-1-piperazinyl}methyl)phenyl]-2-thiophenecarboximidamide;
4(4-{[amino(2-thienyl)methylidene]amino}phenyl)-N-[4-(1,2-dithiolan-3-yl)butyl]-1-piperazinecarboxamide;
4-(4-{[amino(2-thienyl)methylidene]amino}-2-methylphenyl)-N-[4-(1,2-dithiolan-3-yl)butyl]-1-piperazinecarboxamide;

4-(4-{[amino(2-thienyl)methylidene]amino}-3-methylphenyl)-N-[4-(1,2-dithiolan-3-yl)butyl]-1-piperazinecarboxamide;
4-(4-{[amino(2-thienyl)methylidene]amino}-2-methoxyphenyl)-N-[4-(1,2-dithiolan-3-yl)butyl]-1-piperazinecarboxamide;
4-(4-{[amino(2-thienyl)methylidene]amino}-3-methoxyphenyl)-N-[4-(1,2-dithiolan-3-yl)butyl]-1-piperazinecarboxamide;
4-(4-{[amino(2-thienyl)methylidene]amino}-2cyanophenyl)-N-[4-(1,2-dithiolan-3-yl)butyl]-1-piperazinecarboxamide;
4-(3-{[amino(2-thienyl)methylidene]amino}benzyl)-N-[4-(1,2-dithiolan-3-yl)butyl]-1-piperazinecarboxamide;
N'-(3-{4-[5-(1,2-dithiolan-3-yl)pentanoyl]-1-piperazinyl}phenyl)-2-thiophenecarboximidamide;
tert-butyl 5-{[amino(2-thienyl)methylidene]amino}-2-{4-[5-(1,2-dithiolan-3-yl)pentanoyl]-1-piperazinyl}benzylcarbamate;
N'-(3-(aminomethyl)-4-{4-[5-(1,2-dithiolan-3-yl)pentanoyl]-1-piperazinyl}phenyl)-2-thiophenecarboximidamide;
tert-butyl 3-{[-amino(2-thienyl)methylidene]amino}benzyl{1-[5-(1,2-dithiolan-3-yl)pentanoyl]-4-piperidinyl}carbamate;
N'-{3-[({1-[5-(1,2-dithiolan-3-yl)pentanoyl]-4-piperidinyl}amino)methyl]phenyl}-2-thiophenecarboximidamide;
N-[2-(4-{[amino(2-thienyl)methylidene]amino}phenyl)ethyl]-4-{[5-(1,2-dithiolan-3-yl)pentanoyl]amino}benzamide;
and their salts, in particular the corresponding hydrochlorides.

In addition the invention offers a certain number of processes to access the products of general formula (I) described above, the preferred conditions of which processes are described below.

Therefore the invention in particular relates to a process for the preparation of a compound of general formula (I) as defined previously, characterized in that a compound of general formula (II)

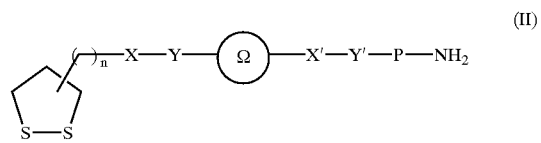

(II)

in which n, X, Y, Ω, X', Y' and P have the same meaning as in general formula (I) is reacted, a) with the compound of general formula (I.i)

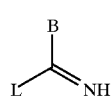

(I.i)

in which B has the same meaning as in general formula (I) and L represents a parting group, for example an alkoxy, alkylthio, sulphonic acid, halide, aryl alcohol or tosyl radical, b) or with the compound of general formula (I.ii)

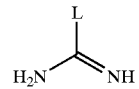

(I.ii)

in which L represents a parting group, for example an alkoxy, alkylthio, sulphonic acid, halide, aryl alcohol or tosyl radical, c) or with the compound of general formula (I.iii)

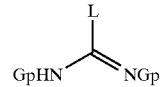

(I.iii)

in which L represents a parting group, for example an alkoxy, alkylthio, sulphonic acid, halide, aryl alcohol or tosyl radical, and Gp a protective group of carbamate type, for example the t-butoxycarbonyl group, this reaction being followed, in the case where the reaction with the compound of general formula (I.iii) is chosen, by hydrolysis in the presence of a strong acid, for example trifluoroacetic acid, d) or with the derivative of formula (I.iv) (N-methyl-N'-nitro-N-nitrosoguanidine)

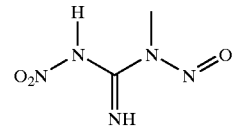

(I.iv)

e) or finally with the derivative of formula (I.v) in which Gp represents a protective group S=.=N—Gp    (I.v)

The invention also relates to a process for the preparation of a product of general formula (I) in which the X—Y group represents —CO—N(R$_3$)—(CH$_2$)$_r$—, characterized in that the acid of general formula (I.vi)

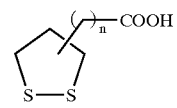

(I.vi)

in which n has the same meaning as in general formula (I), is reacted with an amine of general formula (X) or (Xa)

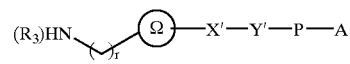

(X)

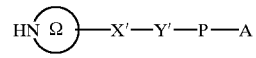

(Xa)

in which r, R$_3$, Ω, X', Y', P and A have the same meaning as in general formula (I), the compound of general formula (Xa) being moreover such that its Ω heterocycle comprises a nitrogen atom.

A subject of the invention is also, as new products, synthesis intermediates useful for the preparation of compounds of general formula (I), namely the compounds of general formulae (II), (III), (IV), (X), (Xa), (XI) and (XIa) as defined above for (II), (X) and (Xa), and further on for (III), (IV), (XI) and (XIa).

In certain cases, the compounds according to the present invention can comprise asymmetrical carbon atoms, and therefore possess two possible enantiomeric forms, i.e. the "R" and "S" configurations. The present invention includes the two enantiomeric forms and all combinations of these forms, including the racemic "RS" mixtures. The present invention includes the two enantiomeric forms and all combinations of these forms, including the racemic "RS" mixtures. For the sake of simplicity, when no specific configuration is indicated in the structural formulae, it should be understood that the two enantiomeric forms and their mixtures are represented.

A subject of the invention is also, as medicaments, the compounds described previously or their pharmaceutically acceptable salts. It also relates to pharmaceutical compositions containing these compounds or their pharmaceutically acceptable salts, and the use of these compounds or of their pharmaceutically acceptable salts for producing medicaments intended to inhibit neuronal NO synthase or inducible NO synthase, to regenerate anti-oxidants, which can be natural or synthetic or to ensure the double function of inhibition of NO synthase and regeneration of anti-oxidants.

By pharmaceutically acceptable salt is meant in particular addition salts of inorganic acids such as hydrochloride, hydrobromide, hydroiodide, sulphate, phosphate, diphosphate and nitrate, or of organic acids, such as acetate, maleate, fumarate, tartrate, succinate, citrate, lactate, methane sulphonate, p-toluenesulphonate, pamoate and stearate. The salts formed from bases such as sodium or potassium hydroxide also fall within the scope of the present invention, when they can be used. For other examples of pharmaceutically acceptable salts, reference can be made to "Salt selection for basic drugs", *Int. J. Pharm.* (1986), 33, 201–217.

A subject of the invention is also the use of a product of general formula (I) or a pharmaceutically acceptable salt of this product for preparing a medicament intended to treat pathologies in which nitrogen monoxide and/or the redox status of the thiol groups are involved, pathologies such as disorders of the central or peripheral nervous system particularly well represented by Parkinson's disease, cerebrovascular disorders, proliferative and inflammatory diseases, vomiting, septic shock, pathologies resulting from radioactive irradiation, solar radiation or organ transplantation, auto-immune and autosomal diseases, cancer and all the pathologies characterised by production or dysfunction involving nitrogen monoxide and/or involving the redox status of the thiol groups.

A subject of the invention is also the use of a product of general formula (I) or of a pharmaceutically acceptable salt of this product, in order to produce a medicament intended to treat cerebro-vascular disorders such as migraine, ischemic or hemorrhagic cerebral infarction, ischemias and thromboses.

Finally a subject of the invention is also the use of a product of general formula (I) or of a pharmaceutically acceptable salt of this product, in order to produce a medicament intended to treat disorders of the central or peripheral nervous system such as for example neurodegenerative diseases, pain and fibromyalgia, cerebral and spinal cord traumas, diabetes and its complications including retinopathies, nephropathies and polyneuropathies, addiction to opiates, alcohol and addictive substances, erective and reproductive disorders, cognitive disorders, encephalopathies, depression, anxiety, schizophrenia, epilepsy, sleeping disorders and alimentary disorders.

The pharmaceutical compositions can be in the form of a solid, for example powders, granules, tablets, capsules, liposomes or suppositories. Appropriate solid supports can be for example calcium phosphate, magnesium stearate, talc, sugars, lactose, dextrin, starch, gelatin, methyl cellulose, sodium carboxymethyl cellulose, polyvinylpyrrolidine and wax.

The pharmaceutical compositions containing a compound of the invention can also be presented in the form of a liquid, for example, solutions, emulsions, suspensions or syrups. Appropriate liquid supports can be, for example, water, organic solvents such as glycerol or glycols, as well as their mixtures, in varying proportions, in water.

A medicament according to the invention can be administered by topical, oral or parenteral route, by intramuscular injection, etc.

The envisaged administration dose for the medicament according to the invention is comprised between 0.1 mg and 10 g according to the type of active compound used.

According to the invention, the compounds of general formula (I) can be prepared by the process described below.

PREPARATION OF THE COMPOUNDS OF THE INVENTION

A) First Approach

The compounds of general formula (I) can be prepared from the intermediates of general formula (II), (III) and (IV) according to Diagram 1 where n, X, X', Y, Y', Ω, P and A are as defined above and Gp is a protective group of carbamate type.

Diagram 1

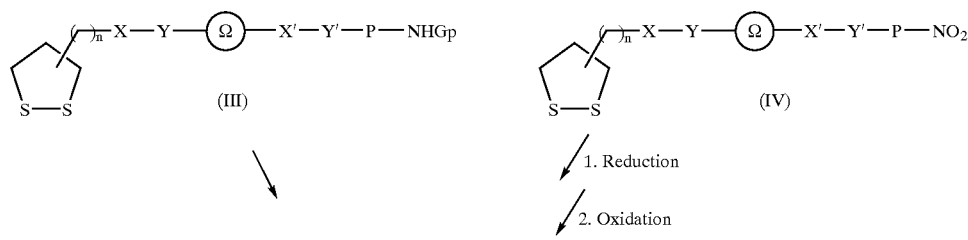

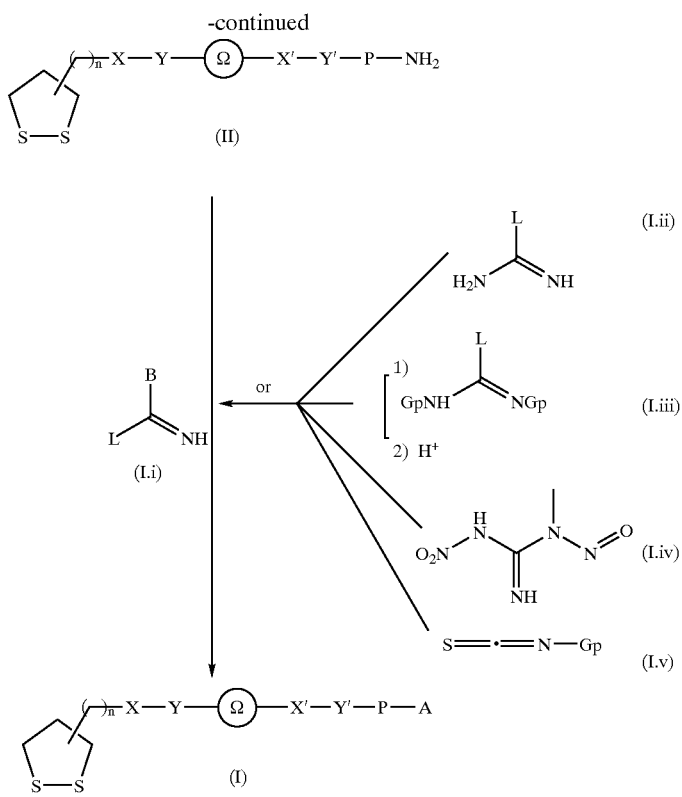

The aniline and amine derivatives of general formula (II), can be condensed with the compounds of general formula (I.i), in which L represents a parting group (in particular an alkoxy, thioalkyl, sulphonic acid, halide, aryl alcohol or tosyl radical), in order to produce the final compounds of general formula (I) of substituted amidine type (cf. Diagram 1). For example, for B=thiophene, the derivatives of general formula (II) can be condensed with S-methylthiophene thiocarboxamide hydroiodide, prepared according to a process in literature (*Ann. Chim.* (1962), 7, 303–337). Condensation can be carried out by heating in an alcohol (for example in methanol or isopropanol), optionally in the presence of DMF at a temperature preferably comprised between 50 and 100° C. for a duration generally comprised between a few hours and overnight.

In the case where B=$SR_{10}$, for example S—$CH_3$, it can be prepared by condensation of the amines or anilines of general formula (II) with the isothiocyanate (I.v) in which Gp represents a protective group such as for example the benzoyl group. Deprotection is then carried out by cleavage of the protective group under appropriate conditions and the thiourea formed is finally treated with, for example, a halogeno alkane in order to produce the final compounds of general formula (I).

In the case where B=$NR_8R_9$, the final compounds of general formula (I) are guanidines. These can be prepared, for example, by condensation of the amines or anilines of general formula (II) with the derivatives of general formula (I.ii) or (I.iii). The reagents of general formula (I.ii) in which L represents, for example, a pyrazole ring are condensed with the amines of general formula (II) according to the conditions described in literature (*J. Org. Chem.* (1992) 57, 2497–2502). Similarly for the reagents of general formula (I.iii) in which L represents, for example, a pyrazole ring and Gp the tBuOCO group (*Tetrahedron Lett.* (1993) 34 (21), 3389–3392) or when L represents the —N—$SO_2$—$CF_3$ group and Gp the tBuOCO group (*J. Org. Chem.* (1998) 63, 3804–3805). During the final stage of synthesis, the deprotection of the guanidine function is carried out in the presence of a strong acid such as for example trifluoroacetic acid.

In the case where B=—$NHNO_2$ the final compounds of general formula (I) can be prepared, for example, by condensation of the amines or anilines of general formula (II) with the reagent of formula (I.iv) (N-methyl-N'-nitro-N-nitrosoguanidine) according to the conditions described in literature (J. Amer. Chem. Soc. (1947), 69, 3028–3030).

The compounds of general formula (I)b, are obtained from the compounds of general formula (I)a where n, X, X', Y, Y', Ω, P and A are as defined above. Conversion of the lipoic compounds of general formula (I)a to the corresponding dihydrolipoic derivatives (I)b where $R_1=R_2=H$ is carried out in alcoholic solvent such as, for example, methanol, in the presence of a reducing agent such as for example $NaBH_4$, $NaBH_3CN$ or lithium aluminium hydride (LAH). The compounds for which $R_1$ and $R_2$ do not both represent H are prepared by reacting the compounds of general formula (I)b with a compound of formula $R_1$-halogen and/or $R_2$-halogen where $R_1$ and $R_2$ are as defined above and the atom halogen is a parting group. The reaction is carried out, for example, in an appropriate solvent such as THF, acetone, ethyl acetate in the presence of a base such as $K_2CO_3$ or triethylamine, in order to produce the compounds of general formula (I)b.

Preparation of the Compounds of General Formula (II):

The intermediates of general formula (II), are obtained from the cleavage of a protective group (Gp) or by reduction of a nitro group.

The intermediates of general formula (II), in which n, X, X', Y, Y', Ω, and P are as defined above, can be prepared from the intermediates of general formula (III) or (IV), Diagram 1, which are compounds comprising respectively a protected amine or aniline (NHGp) in the form, for example, of a carbamate or a nitro group. In the particular case of BOC groups, these are deprotected in a standard fashion using TFA or HCl, in order, finally to produce the primary amines and anilines of general formula (II). Reduction of the nitro function of the intermediates of general formula (IV), Diagram 1, in which n, X, X', Y, Y', Ω, and P are as defined above, is carried out, for example, by heating the product in an appropriate solvent such as ethyl acetate with a little ethanol in the presence of $SnCl_2$ (*J. Heterocyclic Chem.* (1987), 24, 927–930; *Tetrahedron Letters* (1984), 25 (8), 839–842) in the presence of $SnCl_2$/Zn (*Synthesis.* (1996), 9.1076–1078), using $NaBH_4$—$BiCl_3$ (*Synth. Com.* (1995) 25 (23), 3799–3803) in a solvent such as ethanol, or then by using Raney-Ni with added hydrazine hydrate (*Monatshefte für Chemie,* (1995), 126, 725–732), or using indium in a mixture of ethanol and ammonium chloride under reflux (*Synlett* (1998) 9, 1028). Then the product of double reduction is re-oxidized in the presence of ferric chloride ($FeCl_3$) (*Synlett* (1991) 10, 717–718) or iodine (*Tetrahedron Letters.* (1997), 38 (33), 5785–5788) in order to finally produce the amines and anilines of general formula (II) again containing the dithiolane unit.

Preparation of the Compounds of General Formula (III) and (IV):

Synthesis of the Carboxamides of General Formula (III) and (IV):

The carboxamides of general formula (III) and (IV) in which n, X, Y, X', Y', Ω and P are as defined above, which can have either an amide function the nitrogen of which belongs to the Ω heterocycle, or an amide function the nitrogen of which is fixed to the Ω radical or to an alkylene chain linked to this radical, Diagram 2 are prepared by condensation of the acids of general formula (I.vi) with the monoprotected amines or anilines of general formula (VI) and (VIII) or the nitro derivatives of general formula (VII) and (IX). The carboxamide bonds are formed under standard conditions of peptide synthesis (M. Bodanszky and A. Bodanszky, *The Practice of Peptide Synthesis,* 145 (Springer-Verlag, 1984)) in THF, dichloromethane or DMF in the presence of a coupling reagent such as dicyclohexylcarbodiimide (DCC), 1.1'-carbonyldiimidazole (CDI) (*J. Med. Chem.* (1992), 35 (23), 4464–4472) or 1-(3-dimethylaminopropyl)-3-ethylcarbodiimide hydrochloride (EDC or WSCI) (John Jones, *The chemical synthesis of peptides,* 54 (Clarendon Press, Oxford, 1991)) or in the presence of isobutyl chloroformate and N-methyl morpholine (*Org. Prep. Proced. Int.,* (1975), 35, 215). The syntheses of the carboxylic acids of general formula (I.vi) and the amines/anilines of general formula (VI), (VII), (VIII) and (IX) which are not commercially available, are described below.

Diagram 2

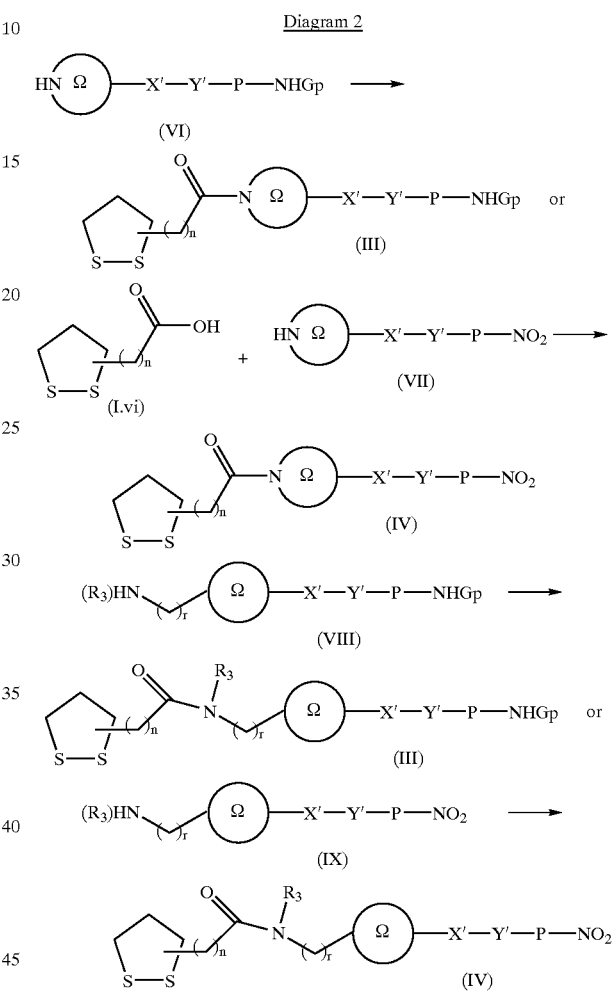

B) Second Approach

The compounds of general formula (I) can also be prepared from the intermediates of general formula (X), (XI), (XII) and (XIII) (or (Xa), (XIa), (XIIa) and (XIIIa) when the amine function forms part of the Ω heterocycle) according to Diagram 3 in which n, X, X', Y, Y', Ω, P and A are as defined above and $Gp_1$ and $Gp_2$ are protective groups: for example, when Y=—$NR_3$—, $Gp_1$ can be a protective group of carbamate type or when Y=—O—, $Gp_1$ can be a protective group of benzyl type or other protective groups ($Gp_1$) known to a person skilled in the art. $Gp_2$ can also be a protective group of carbamate type or other protective groups ($Gp_2$) known to a person skilled in the art.

Diagram 3

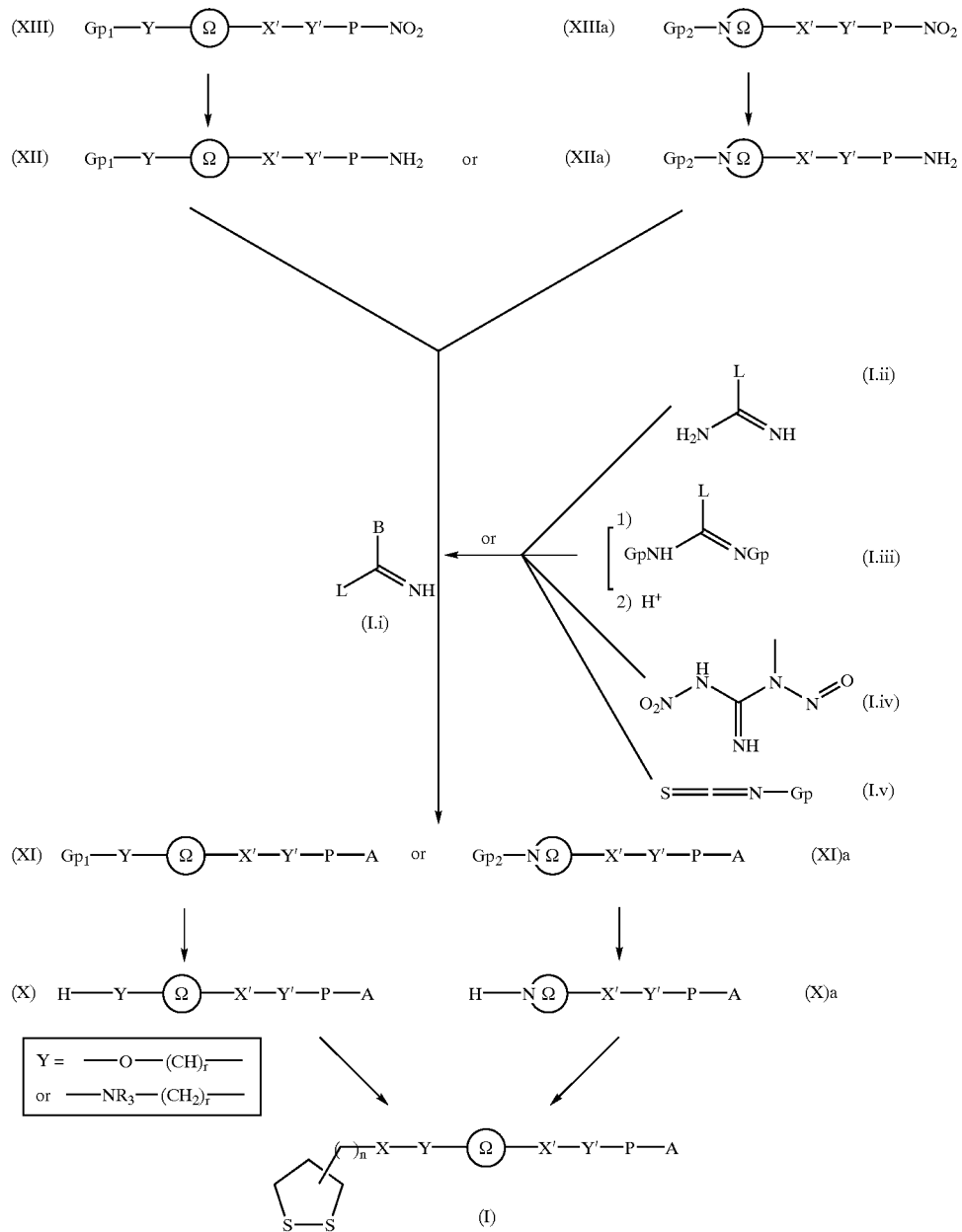

Preparation of the Compounds of General Formula (I):
Synthesis of the Carboxamides of General Formula (I):

The carboxamides of general formula (I), Diagram 4, in which n, X',Y', Ω, P and A are as defined above, are prepared by condensation of the acids of general formula (I.vi) with the amines/anilines of general formula (X) and (X)a. The carboxamide bonds are formed under standard conditions of peptide synthesis (M. Bodanszky and A. Bodanszky, *The Practice of Peptide Synthesis*, 145 (Springer-Verlag, 1984)) in THF, dichloromethane or DMF, in the presence of a coupling reagent such as dicyclohexylcarbodiimide (DCC), 1.1'-carbonyldiimidazole (CDI) (*J. Med. Chem.* (1992), 35 (23), 4464–4472) or 1-(3-dimethylaminopropyl)-3-ethylcarbodiimide hydrochloride (EDC or WSCI) (John Jones, The chemical synthesis of peptides, 54 (Clarendon Press, Oxford, 1991)) or in the presence of isobutyl chloroformate and N-methyl morpholine (*Org. Prep. Proced. Int.*, (1975), 35, 215). The syntheses of the carboxylic acids of general formula (I.vi) which are not commercially available, are described below.

Diagram 4

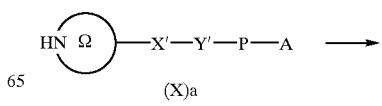

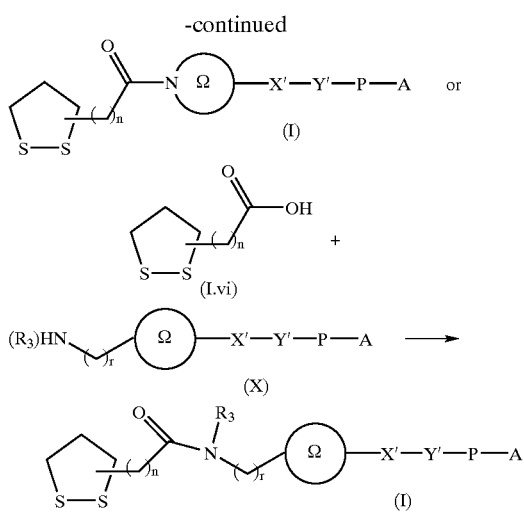

Synthesis of the Ureas of General Formula (I)

The ureas of general formula (I), Diagram 5, in which n, X',Y', Ω, P and A are as defined above, are prepared, for example, by condensation of the acids of general formula (I.vi) with the amines/anilines of general formula (X) and (X)a in toluene in the presence of diphenylphosphoryl azide (DPPA) and triethylamine, for example at a temperature of 80° C. and for 2 to 3 hours.

Diagram 5

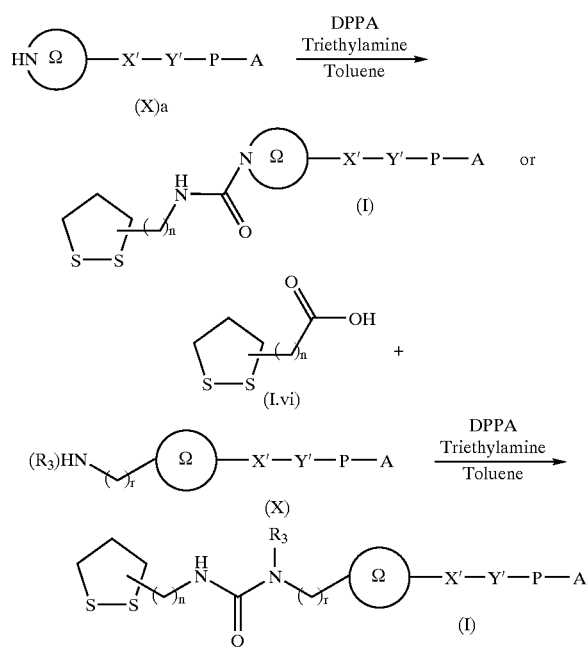

Preparation of the Compounds of General Formula (X), (X)a, (XI), (XI)a, (XII), (XII)a, (XIII) and (XIII)a:

The compounds of general formula (X) and (X)a are obtained from the cleavage of a protective group. The compounds of general formula (X) and (X)a, in which X', Y, Y', Ω, P and A are as defined above, can be prepared from the compounds of general formula (XI) and (XI)a, Diagram 3, which are compounds comprising a protected amine/aniline (NHGp) in the form, for example, of a carbamate or an alcohol or phenol protected by a benzyl group (O-benzyl) or by other protective groups ($Gp_1$, $Gp_2$) known to a person skilled in the art. In the particular case of the BOC groups, these are deprotected in a standard fashion using trifluoroacetic acid (TFA) or HCl, the O-benzyl groups being themselves deprotected in a standard fashion by catalytic hydrogenation in the presence of Pd on carbon, and the compounds of general formula (X) and (X)a are finally obtained.

The compounds of general formula (XI) and (XI)a can be prepared from the intermediates of general formula (XII) and (XII)a and (XIII) and (XIII)a according to Diagram 3 where Ω, Y, X', Y', P are as defined above and $Gp_1$ and $Gp_2$ are protective groups.

The aniline/amine derivatives of general formula (XII) and (XII)a can be condensed with compounds of general formula (I.i, Iii, and Iiii), in which L represents a parting group and with (I.iv and I.v) as previously described for the compounds of general formula (I) in Diagram 1, in order to finally produce to the compounds of general formula (X) and (X)a, Diagram 3.

The compounds of general formula (XII) and (XII)a, are obtained from the reduction of a nitro group of the compounds of general formula (XIII) and (XIII)a. Reduction of the nitro function of the compounds of general formula (XIII) and (XIII)a, Diagram 3, in which Ω, Y, X', Y' and P are as defined above, is carried out, for example, in a standard fashion by catalytic hydrogenation in the presence of Pd on carbon, or by heating the product in an appropriate solvent such as ethyl acetate with a little ethanol in the presence of $SnCl_2$ (*J. Heterocyclic Chem.* (1987), 24, 927–930; *Tetrahedron Letters* (1984), 25 (8), 839–842), in the presence of $SnCl_2$/Zn (*Synthesis.* (1996),9.1076–1078) or also using $NaBH_4$—$BiCl_3$ (*Synth. Com.* (1995) 25 (23), 3799–3803) in a solvent such as ethanol, or then by using Raney-Ni with added hydrazine hydrate (*Monatshefte für Chemie,* (1995), 126, 725–732), or finally using indium in a mixture of ethanol and ammonium chloride under reflux (*Synlett* (1998) 9, 1028), in order to finally produce the primary amines and anilines of general formula (XII) and (XII)a.

The synthesis of the compounds of general formula (XIII) and (XIII)a which are not commercially available, is described below.

Preparation of Certain Synthesis Intermediates Which are not Commercially Available:

The acids of general formula (I.vi) which are not commercially available, in which m is as defined above are accessible from processes in literature. For example, trisnorlipoic acid [2-(1,2-dithiolan-3-yl)-acetic acid] is obtained in 5 stages according to an experimental protocol described in *Tetrahedron Letters.*(1997), 38 (33), 5785–5788.

The compounds of general formula (XIII)a in which P represents a phenylene radical, Ω represents a piperazinyl or homopiperazinyl radical (T represents the —$(CH_2)_x$— radical with x=2 or 3) and r and $R_6$ are as defined in general formula (I), Diagram 3.1, are prepared from the halogenated derivatives of general formula (XIII.1)a. The latter are subjected to a nucleophilic substitution by a heterocyclic compound of general formula (XIII.2)a in a solvent such as DMSO, DMF, acetone or dichloromethane in the presence of a base such as $K_2CO_3$, KOH, NaOH or triethylamine, in order to produce the intermediates of general formula (XIII) a.

Diagram 3.1

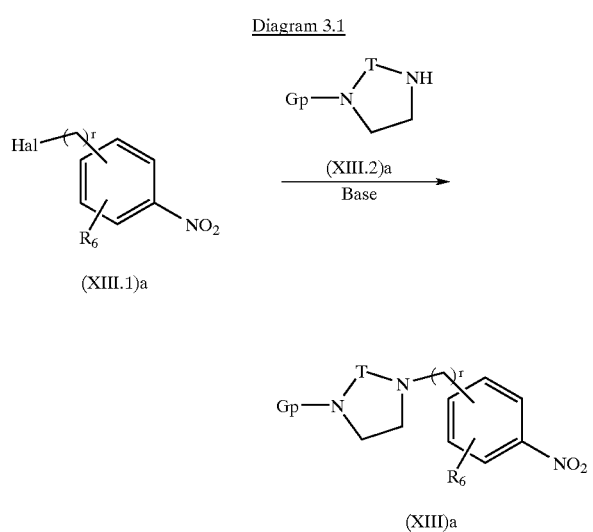

Certain compounds of general formula (XIII)a in which P represents a phenylene radical, Ω represents a piperidine, homopiperidine or pyrrolidine radical (T represents the —(CH$_2$)$_y$— radical with y=1, 2 or 3) and R$_6$ is as defined in general formula (I) can be prepared, Diagram 3.2, from the substituted nitrobenzaldehydes of general formula (XIII.3)a. The substituted compounds of general formula (XIII.3)a are condensed with an amine of general formula (XIII.4)a in reducing medium. The reaction takes place in alcoholic solvent such as, for example, methanol, in the presence of a reducing agent such as, for example, NaBH$_4$ or NaBH$_3$CN. When R$_3$=H, the protection of the free amine function of the compounds of general formula (XIII)a, is carried out in a standard fashion with (Boc)$_2$ in dichloromethane or by other protection techniques known to a person skilled in the art.

The compounds of general formula (XIII)a in which P represents a phenylene radical, Ω represents a piperazinyl or homopiperazinyl radical (T represents the —(CH$_2$)$_z$— radical with z=2 or 3), r is as defined above and R$_6$ is an aminomethyl radical protected by a protective group Gp$_2$, Diagram 3.3, are prepared from the halogenated derivatives of general formula (XIII.5)a. The reduction of the nitrile function of the intermediates of general formula (XIII.6)a is carried out, for example, in an appropriate solvent such as ether or THF, in the presence of a reducing agent such as for example diborane. The protection of the primary amine formed is then carried out in a standard fashion with (Boc)$_2$ in dichloromethane or by other protection techniques known to a person skilled in the art in order to produce the compounds of general formula (XIII)a.

Diagram 3.2 / Diagram 3.3

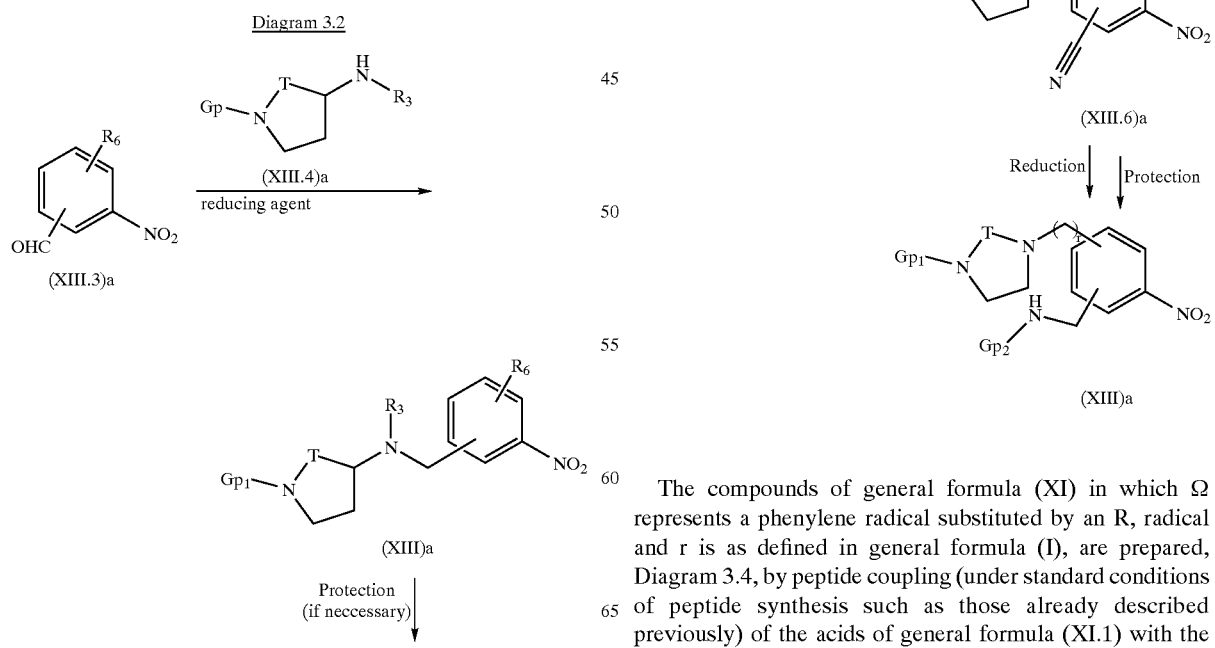

The compounds of general formula (XI) in which Ω represents a phenylene radical substituted by an R, radical and r is as defined in general formula (I), are prepared, Diagram 3.4, by peptide coupling (under standard conditions of peptide synthesis such as those already described previously) of the acids of general formula (XI.1) with the amines of general formula (XI.2). Preparation of the amines of general formula (XI.2) can be carried out, for example, in a similar manner with the operating method of Stages 17.2 to 17.6 of Example 17 described below. The $R_5$ group is optionally protected beforehand when it comprises an amine, aniline, alcohol or free phenol function, the deprotection of said amine, aniline, alcohol or free phenol function having in principle taken place once the peptide coupling reaction between the compound of general formula (I.vi) and the compound of general formula (X) is carried out (these reactions, carried out according to current processes for a person skilled in the art, are not indicated in Diagram 3.4).

Diagram 3.4

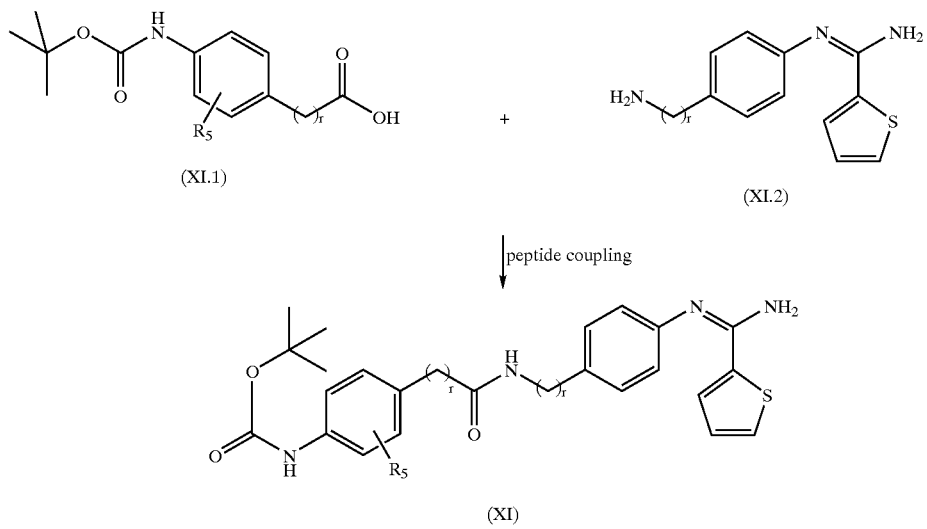

Unless otherwise specified, all the technical and scientific terms used here have the same meaning as that commonly understood by an ordinary specialist in the field to which the invention belongs. Similarly, all publications, patent applications, all patents and all other references mentioned here are incorporated by way of reference.

The following examples are presented to illustrate the above procedures and must in no case be considered as a limit to the scope of the invention.

EXAMPLES

Example 1

N'-(4-{4-[5-(1,2-dithiolan-3-yl)pentanoyl]-1-piperazinyl}phenyl)-2-thiophenecarboximidamide hydrochloride A. Process According to the First Approach:

1.A.1) 1-[5-(1,2-dithiolan-3-yl)pentanoyl]-4-(4-nitrophenyl)piperazine:

5.0 g (24.13 mmol) of nitrophenylpiperazine, triethylamine (14.0 ml), 4.24 g (31.37 mmol) hydroxybenzotriazole and 12.0 g (62.73 mmol) 1-(3-dimethylaminopropyl)-3-ethyl-carbodiimide hydrochloride are added successively to a solution of 5.0 g (24.13 mmol) (DL)-thioctic acid in 120 ml of dichloromethane. After having stirred the reaction mixture overnight at 25° C., the mixture is diluted with 400 ml of water and the stirring is maintained for an additional 30 minutes. The product is extracted using 3 times 200 ml of dichloromethane. The organic solution is dried over magnesium sulphate, filtered and concentrated under vacuum. The solid obtained is filtered and rinsed with diethyl ether in order to obtain, after drying, 6.21 g of a yellow solid product with a yield of 65%. Melting point: 97.6–98.5° C.

1.A.2) 4-{4-[5-(1,2-dithiolan-3-yl)pentanoyl]-1-piperazinyl}aniline:

16 ml of a saturated aqueous solution of ammonium chloride and 21.0 g (0.183 mol) of powdered Indium is added successively to a solution of 5.2 g (13.20 mmol) of intermediate 1.A.1 in 60 ml of ethanol then the reaction medium is taken to reflux for 5 hours (*Synlett* (1998) 9, 1028). The mixture is cooled down to ambient temperature and filtered on celite. The filtrate is alkalinized to pH 10 with a 50% solution of sodium hydroxide. The reduced product is extracted using 4 times 150 ml of dichloromethane. The organic solution is dried over magnesium sulphate, followed by filtration and concentration under vacuum in order to produce a yellow oil. The oil is dissolved in a mixture of 15 ml of dimethylformamide and 20 ml of ethyl acetate. The medium is cooled down using an ice bath, to 0° C., and a 10% aqueous solution of potassium bicarbonate is added dropwise. After having stirred the reaction mixture for approximately 10 minutes at 0° C., iodine solution (3.45 g in 40 ml of ethyl acetate) is added dropwise until the iodine colouration remains. The product is extracted using 4 times 100 ml of ethyl acetate, the organic solution is dried over magnesium sulphate, followed by filtration and concentration under vacuum. Purification on a silica column (eluent= 5% ethanol in dichloromethane) is then carried out in order to produce a yellow oil, 3.03 g, with a yield of 63%.

MH$^+$=366.2. NMR $^1$H (DMSO d6, 400 MHz, δ): 1.39 (m, 2H, CH$_2$); 1.50–1.70 (m, 4H, CH$_2$); 1.87 (m, 1H, CH$_2$); 2.32 (m, 2H, CH$_2$); 2.34 (m, 1H, CH$_2$); 2.80–2.88 (m, 4H, CH$_2$-piperazine); 3.17 (m, 2H, CH$_2$); 3.53 (m, 4H, CH$_2$-piperazine); 3.59 (m, 1H, —S—CH—); 4.58 (s, 2H, NH$_2$); 6.50 (d, 2H, arom., J=7.0 Hz); 6.69 (d, 2H, arom., J=7.0 Hz).

1.A.3) N'-(4-{4-[5-(1,2-dithiolan-3-yl)pentanoyl]-1-piperazinyl}phenyl)-2-thiophenecarboximidamide hydrochloride:

Intermediate 1.A.2 (0.5 g; 1.36 mmol) is dissolved in 2-propanol (15 ml) and 0.582 g of S-methyl-2-thiophene thiocarboximide hydroiodide (2.04 mmol) (*Ann. Chim.,*

(1962), 7, 303–337) is added. After stirring at 25° C. for 15 hours, the reaction mixture is concentrated to dryness under vacuum. The residue is taken up in dichloromethane and a saturated aqueous solution of NaHCO₃. After decantation, the organic phase is washed successively with 50 ml of a saturated solution of NaHCO₃, with water then with salt water. The organic solution is dried over magnesium sulphate, followed by filtration and evaporation under reduced pressure. Then the free base is dissolved in 5 ml of ethanol and the solution is cooled down using an ice bath before the dropwise addition of 0.3 ml of a 1N solution of HCl in anhydrous ethyl ether. After stirring for 15 hours at 25° C., the crystals obtained are filtered and rinsed in diethyl ether in order to obtain after drying 0.320 g of a yellow solid product with a yield of 43%. Melting point: 203–203.7° C.

B. Process According to the Second Approach:

1.B.1) tert-butyl 4-(4-nitrophenyl)-1-piperazinecarboxylate 5.55 g (26.5 mmol) of 1-(4-nitrophenyl)piperazine is dissolved in a mixture of 60 ml of dichloromethane and 8.2 ml of triethylamine. The medium is cooled down using an ice bath before the addition of 6.4 g (29.2 mmol) of (Boc)₂O in several portions. The reaction mixture is stirred at 23° C. for 12 hours and poured into a water-ice mixture. The organic phase is decanted, washed successively with 20 ml of water and 20 ml of salt water. After drying over sodium sulphate, filtration and concentration under vacuum, then trituration with isopropyl ether, a yellow solid is obtained with a quantitative yield. Melting point: 143.7–145.7° C.

1.B.2) tert-butyl 4-(4-aminophenyl)-1-piperazinecarboxylate

A solution of intermediate 1.B.1 (7.63 g; 25.0 mmol) in 40 ml of a dichloromethane/ethanol mixture (30 ml/50 ml) as well as 1.0 g of 10% Pd/C is introduced into a stainless steel autoclave provided with a magnetic stirrer. The reaction mixture is stirred under hydrogen pressure (1.5 bars) for 12 hours at a temperature of 20° C. The Pd/C is then eliminated by filtration and the filtrate is concentrated under vacuum. The evaporation residue is purified by trituration with ether, a grey powder is obtained (4.96 g; yield 71%). Melting point: 145° C.

1.B.3) tert-butyl 4-(4-{[amino(2-thienyl)methylidene]amino}phenyl)-1-piperazinecarboxylate Intermediate 1.B.2 (4.96 g; 17.9 mmol) is dissolved in 2-propanol (150 ml) and 7.66 g of S-methyl-2-thiophene thiocarboxamide hydroiodide (26.8 mmol) (Ann. Chim., (1962), 7, 303–337) is added. After stirring at 25° C. for 15 hours, the reaction mixture is concentrated to dryness under vacuum. The residue is taken up in dichloromethane and a saturated aqueous solution of NaHCO₃. After decantation, the organic phase is washed successively with 50 ml of a saturated solution of NaHCO₃, water and salt water. The organic solution is dried over magnesium sulphate, followed by filtering and evaporating under reduced pressure. The solid obtained is filtered and rinsed in isopentane in order to obtain, after drying, 6.91 g of a yellow solid product (yield 78%). Melting point: 164° C.

1.B.4) N'-[4-(1-piperazinyl)phenyl]-2-thiophenecarboximidamide:

A stream of HCl gas is passed bubblewise through a solution at 0° C. of intermediate 1.B.3 (5.40 g; 14.0 mmol) in ethyl acetate (200 ml). The mixture is left to return to ambient temperature overnight. A stream of argon is passed through the reaction mixture, then the powder obtained is filtered and washed with ethyl acetate in order to produce a white-beige solid (5.0 g; yield 99%). Melting point: 180° C.

1.B.5) N'-(4-{4-[5-(1,2-dithiolan-3-yl)pentanoyl]-1-piperazinyl}phenyl)-2-thiophenecarboximidamide hydrochloride:

The experimental protocol used is similar to that described for compound 1.A.1. The hydrochloride is produced in the same way as for intermediate 1.A.3. The expected yellow solid is obtained.

Example 2

N'-(4-{4-[2-(1,2-dithiolan-3-yl)acetyl]-1-piperazinyl}phenyl)-2-thiophenecarboximidamide The experimental protocol used is the same as that described for compound 1, process A. Norlipoic acid, (*Tetrahedron Letters* (1997), 38 (33), 5785–5788), replacing lipoic acid, in order to produce a yellow solid (0 acid.126 g).

MH⁺=433.2. NMR ¹H (DMSO d6, 400 MHz, δ): 1.97 (m, 1H, CH₂); 2.40 (m, 1H, CH₂); 2.75 (m, 1H,CH₂); 2.87 (m, 1H,CH₂); 3.04 (m, 4H, CH₂-piperazine); 3.09 (m, 1H,CH₂); 3.21 (m, 1H, CH₂); 3.59 (m, 4H, CH₂-piperazine); 3.97 (m, 1H, —S—CH—); 6.26 (broad s, 2H, NH₂); 6.76 (d, 2H, arom., J=8.6 Hz); 6.94 (d, 2H, arom., J=8.6 Hz); 7.07 (m, 1H,CH-thiophene); 7.57 (m, 1H,CH-thiophene); 7.70 (m, 1H,CH-thiophene).

Example 3

N'-[3-({4-[5-(1,2-dithiolan-3-yl)pentanoyl]-1-piperazinyl}methyl)phenyl]-2-thiophenecarboximidamide hydrochloride The experimental protocol used is the same as that described for compound 1, process A. A white solid (0.220 g) is obtained. Melting point: 240.0–240.5° C.

Example 4

N'-[3-({4-[2-(1,2-dithiolan-3-yl)acetyl]-1-piperazinyl}methyl)phenyl]-2-thiophenecarboximidamide The experimental protocol used is the same as that described for compound 1, process A. Norlipoic acid, (*Tetrahedron Letters* (1997), 38 (33), 5785–5788), replacing lipoic acid, in order to produce a yellow foam (0.20 g).

MH⁺=447.2. NMR ¹H (DMSO d6, 400 MHz, δ): 1.96 (m, 1H, CH₂); 2.34–2.40 (m, 4H, CH₂-piperazine); 2.49 (m, 1H, CH₂); 2.71 (m, 1H,CH₂); 2.80 (m, 1H, CH₂); 3.08 (m, 1H, CH₂); 3.28 (m, 1H, CH₂); 3.41 (m, 4H, CH₂-piperazine); 3.46 (3, 2H, CH₂); 3.93 (m, 1H, —S—CH—); 6.54 (broad s, 2H, NH₂); 6.77 (d, 1H, arom., J=7.60 Hz); 6.82 (s, 1H, arom); 6.95 (d, 1H, arom., J=7.60 Hz); 7.10 (m, 1H,CH-thiophene); 7.26 (t, 1H, arom., J=7.60 Hz); 7.63 (m, 1H, CH-thiophene); 7.74 (m, 1H, CH-thiophene).

Example 5

4-(4-{[amino(2-thienyl)methylidene]amino}phenyl)-N-[4-(1,2-dithiolan-3-yl)butyl]-1-piperazinecarboxamide 0.206 g (1.0 mmol) of lipoic acid is solubilized under an argon atmosphere in dioxane (5 ml), acetonitrile (5 ml) and triethylamine (0.3 ml). Diphenylphosphoryl azide (0.24 ml; 1.0 mmol) is added, then the reaction medium is taken to 80° C. for 2 hours. The reaction medium is then cooled down using an ice bath, then intermediate 1.B.4 (0.395 g; 1.0 mmol) is added. After having stirred the reaction mixture overnight at 25° C., the mixture is diluted with 100 ml of water and stirring is continued for another 30 minutes. The product is extracted using 3 times 25 ml of ethyl acetate. The organic solution is dried over magnesium sulphate, filtered and concentrated under vacuum. Purification on a silica column (eluent=10% of ethanol in dichloromethane) is then carried out in order to produce a yellow solid. The yellow solid is further purified by recrystallization from ethanol in order to produce 0.25 g of product (yield 46.4%). Melting point: 201.1–201.8° C.

Example 6

4-(4-{[amino(2-thienyl)methylidene]amino}-2-methylphenyl)-N-[4-(1,2-dithiolan-3-yl)butyl]-1-piperazinecarboxamide 6.1. tert-butyl 4-(2-methyl-4-nitrophenyl)-1-piperazinecarboxylate 4.65 g (3.10 mmol) of 2-fluoro-5-nitrotoluene, 6.71 g (3.60 mmol) of tert-butyl 1-piperazinecarboxylate and 10.4 g (7.50 mmol) of potassium carbonate are solubilized under an argon atmosphere, in dry DMF (50 ml), then the reaction medium is taken to 80° C. for 18 hours. The reaction medium is then cooled down using an ice bath then poured into ice-cold water. The product is extracted using 3 times 50 ml of ethyl acetate. The organic solution is dried over magnesium sulphate, followed by filtration and concentration under vacuum. Purification is then carried out by crystallization from diisopropyl ether and the solid obtained is filtered and rinsed with isopentane in order to obtain, after drying, 5.9 g of a yellow solid product (yield 62%). Melting point: 121.8–123.4° C.

6.2. tert-butyl 4-(4-amino-2-methylphenyl)-1-piperazinecarboxylate

The experimental protocol used is the same as that described for compound 1.B.2. intermediate, 6.1 replacing intermediate 1.B.1 and ethanol replacing the dichloromethane/ethanol mixture in order to produce a beige foam which is sufficiently pure to be used in the following stage (yield 98%)

MH$^+$=292.20.

6.3. tert-butyl 4-(4-{[amino(2-thienyl)methylidene]amino}-2-methylphenyl)-1-piperazinecarboxylate The experimental protocol used is the same as that described for compound 1.B.3., intermediate 6.2 replacing intermediate 1.B.2. After purification by crystallization from ether, the solid obtained is filtered and rinsed with diisopropyl ether, in order to obtain, after drying, a pale white-yellow solid product (yield 71%). Melting point: 165° C.

6.4. N'-[3-methyl-4-(1-piperazinyl)phenyl]-2-thiophenecarboximidamide hydrochloride The experimental protocol used is the same as that described for compound 1.B.4., intermediate 6.3 replacing intermediate 1.B.3. A white-coloured solid-foam product is obtained (yield 95%).

MH$^+$=301.20.

6. 5. 4-(4-{[-amino(2-thienyl)methylidene]amino}-2-methylphenyl)-N-[4-(1,2-dithiolan-3-yl)butyl]-1-piperazinecarboxamide The experimental protocol used is the same as that described for the compound of Example 5, intermediate 6.4 replacing intermediate 1.B.4. A yellowish-white solid product is obtained (yield 3%). Melting point: 193.3–194.6° C.

Example 7

4-(4-{[amino(2-thienyl)methylidene]amino}-3-methylphenyl)-N-[4-(1,2-dithiolan-3-yl)butyl]-1-piperazinecarboxamide The experimental protocol used is the same as that described for the compound of Example 6, 5-fluoro-2-nitrotoluene replacing 2-fluoro-5-nitrotoluene. A white solid product is obtained (yield 16%). Melting point: 169.4–170.9° C.

Example 8

4-(4-{[amino(2-thienyl)methylidene]amino}-2-methoxyphenyl)-N-[4-(1,2-dithiolan-3-yl)butyl]-1-piperazinecarboxamide The experimental protocol used is the same as that described for the compound of Example 6, 2-chloro-5-nitroanisole replacing 2-fluoro-5-nitrotoluene. A pale yellow solid product is obtained (yield 25%). Melting point: 185.6–186.3° C.

Example 9

4-(4-{[amino(2-thienyl)methylidene]amino}-3-methoxyphenyl)-N-[4-(1,2-dithiolan-3-yl)butyl]-1-piperazinecarboxamide The experimental protocol used is the same as that described for the compound of Example 6, 5-chloro-2-nitroanisole replacing 2-fluoro-5-nitrotoluene. A pale yellow foam is obtained (yield 4%).

MH$^+$=520.20.

Example 10

4-(4-{[amino(2-thienyl)methylidene]amino}-2-cyanophenyl)-N-[4-(1,2-dithiolan-3-yl)butyl]-1-piperazinecarboxamide The experimental protocol used is the same as that described for the compound of Example 6, 2-fluoro-5-nitrobenzonitrile replacing 2-fluoro-5-nitrotoluene. A yellow solid is obtained (yield 12%).

MH$^+$=515.30.

Example 11

4-(3-{[amino(2-thienyl)methylidene]amino}benzyl)-N-[4-(1,2-dithiolan-3-yl)butyl]-1-piperazinecarboxamide 11.1. tert-butyl 4-(3-nitrobenzyl)-1-piperazinecarboxylate 5.00 g (2.30 mmol) of 3-nitrobromobenzyl and 4.53 g (2.40 mmol) of tert-butyl 1-piperazinecarboxylate are solubilized, under an argon atmosphere, in dichloromethane (100 ml), then triethylamine (8 ml) is added dropwise. The reaction medium is stirred overnight at ambient temperature before being poured into ice-cold water. The product is extracted using 3 times 150 ml of dichloromethane. The organic solution is dried over magnesium sulphate, followed by filtration and concentration under vacuum. Purification is then carried out on a silica column (eluent=gradient ranging from pure heptane to pure ethyl acetate) in order to produce a yellow oil. After cold crystallization, 6.2 g of a yellow solid is obtained (yield 84%). Melting point: 85.5° C.

11.2. tert-butyl 4-(3-aminobenzyl)-1-piperazinecarboxylate

The experimental protocol used is the same as that described for compound 1.A.2, intermediate 11.1 replacing intermediate 1.A.1. A yellow oil is obtained which, after cold crystallization, produces a yellow solid (yield 98%). Melting point: 102.3° C.

11.3. Hydroiodide of tert-butyl 4-(3-{[amino(2-thienyl)methylidene]amino}benzyl)-1-piperazinecarboxylate.

The experimental protocol used is the same as that described for compound 1.B.3, intermediate 11.2 replacing intermediate 1.B.2. A white solid is obtained. Melting point: 161.4° C.

11.4. N'-[3-(1-piperazinylmethyl)phenyl]-2-thiophenecarboximidamide

The experimental protocol used is the same as that described for compound 1.B.4, intermediate 11.3 replacing intermediate 1.B.3. A hygroscopic yellow solid is obtained (yield 72%).

MH+=301.10.

11.5. 4-(3-{[amino(2-thienyl)methylidene]amino}benzyl)-N-[4-(1,2-dithiolan-3-yl)butyl]-1-piperazinecarboxamide The experimental protocol used is the same as that described for the compound of Example 5, intermediate 11.4 replacing intermediate 1.B.4. A pale yellow solid is obtained (yield 2%). Melting point: 152.0–153.4° C.

Example 12

N'-(3-{4-[5-(1,2-dithiolan-3-yl)pentanoyl]-1-piperazinyl}phenyl)-2-thiophenecarboximidamide 12.1. tert-butyl 4-(3-nitrophenyl)-1-piperazinecarboxylate 5.0 g (3.54 mmol) of 1-fluoro-3-nitrotoluene, 9.89 g (5.31 mmol) of tert-butyl 1-piperazinecarboxylate and 27.0 g (19.5 mmol) of potassium carbonate are solubilized under an argon atmosphere in DMSO (60 ml), then the reaction medium is taken to 100° C. for 72 hours. The reaction medium is then cooled down using an ice bath then poured into ice-cold water. The product is extracted using 3 times 50 ml of dichloromethane. The organic solution is dried over magnesium sulphate, followed by filtration and concentration under vacuum. Purification on a silica column is then carried out (eluent=heptane 70%/ethyl acetate 30%) in order to produce a yellow solid. The yellow solid is further purified by recrystallization from diisopropyl ether in order to produce 4.5 g of the expected product (yield 42.0%). Melting point: 82.0–92.0° C.

12.2. tert-butyl 4-(3-aminophenyl)-1-piperazinecarboxylate

The experimental protocol used is the same as that described for compound 1.B.2, intermediate 13.1 replacing intermediate 1.B.1 and a dichloromethane/THF mixture (50/50) replacing the dichloromethane/ethanol mixture. After purification by crystallization from diisopropyl ether, a white solid is obtained (yield 25%). Melting point: 218.0° C.

12.3. tert-butyl 4-(3-{[amino(2-thienyl)methylidene]amino}phenyl)-1-piperazinecarboxylate The experimental protocol used is the same as that described for compound 1.B.3, intermediate 13.2 replacing intermediate 1.B.2. A pale yellow solid is obtained (yield 58%). Melting point: 150.0° C.

12.4.) N'-[3-(1-piperazinyl)phenyl]-2-thiophenecarboximidamide hydrochloride

The experimental protocol used is the same as that described for compound 1.B.4, intermediate 13.2 replacing intermediate 1.B.3. A yellow-beige coloured solid is obtained (yield 88%). Melting point: 141.4° C.

12.5. N'-(3-{4-[5-(1,2-dithiolan-3-yl)pentanoyl]-1-piperazinyl}phenyl)-2-thiophenecarboximidamide The experimental protocol used is similar to that described for compound 1.A.1, intermediate 13.3 replacing the nitrophenylpiperazine. The expected product is obtained in the form of light yellow foam (yield 63%).

MH+=475.20.

Example 13 tert-butyl 5-{[amino(2-thienyl)methylidene]amino}-2-{4-[5-(1,2-dithiolan-3-yl)pentanoyl]-1-piperazinyl}benzylcarbamate 13.1. 2-(4-benzyl-1-piperazinyl)-5-nitrobenzonitrile The experimental protocol used is the same as that described for compound 6.1, 2-fluoro-5-nitrobenzonitrile replacing 2-fluoro-5-nitrotoluene and 1-benzylpiperazine replacing tert-butyl 1-piperazinecarboxylate. A light ochre-coloured solid is obtained (yield 89%). Melting point: 124.0° C.

13.2. [2-(4-benzyl-1-piperazinyl)-5-nitrophenyl]methanamine 3.90 g (1.21 mmol) of intermediate 14.1 is solubilized under an argon atmosphere in dry THF (40 ml) and a solution of diborane (1M in THF; 24.2 ml; 2.42 mmol) is added dropwise before taking the resulting mixture to reflux for 18 hours. Methanol (5 ml) is added followed by stirring. HCl gas is then allowed to bubble through the reaction medium. After evaporation to dryness of the mixture, the residue is diluted with water (50 ml), the solution is rendered alkaline with sodium bicarbonate (10%) and extracted with dichloromethane (3 times 100 ml). The organic solution is then dried over magnesium sulphate, followed by filtration and concentration under vacuum. Purification is then carried out on a silica column (eluent=dichloromethane containing 5% of ethanol) in order to produce a brown oil (yield 42.0%).

MH+=327.20.

13.3. tert-butyl 2-(4-benzyl-1-piperazinyl)-5-nitrobenzylcarbamate

The experimental protocol used is the same as that described for compound 1.B.1, intermediate 14.2 replacing the 1-(4-nitrophenyl)piperazine and diisopropylethylamine replacing the triethylamine. After purification on a silica column (eluent=dichloromethane containing 5% ethanol) a yellow oil (yield 91.0%) is produced.

MH+=427.20.

13.4. tert-butyl 5-amino-2-(1-piperazinyl)benzylcarbamate

The experimental protocol used is the same as that described for compound 1.B.2, intermediate 14.3 replacing intermediate 1.B.1 and a dichloromethane/THF mixture (50/50) replacing the dichloromethane/ethanol mixture. A white foam is obtained which is sufficiently pure to be used in the following stage (yield 95%).

MH+=307.20.

13.5. tert-butyl 5-{[amino(2-thienyl)methylidene]amino}-2-(1-piperazinyl)benzylcarbamate The experimental protocol used is the same as that described for compound 1.B.3, intermediate 14.4 replacing intermediate 1.B.2 whilst two equivalents of dried pyridine are added to the reaction medium. A yellow foam is obtained after treatment, which is sufficiently pure to be used in the following stage (yield 49%).

MH+=416.20.

13.6. tert-butyl 5-{[amino(2-thienyl)methylidene]amino}-2-{4-[5-(1,2-dithiolan-3-yl)pentanoyl]-1-piperazinyl}benzylcarbamate The experimental protocol used is similar to that described for compound 1.A.1, intermediate 13.5 replacing the nitrophenylpiperazine. The expected product is obtained in the form of a white solid (yield 45%). Melting point: 162.4–164.0° C.

Example 14

N'-(3-(aminomethyl)-4-{4-[5-(1,2-dithiolan-3-yl)pentanoyl]-1-piperazinyl}phenyl)-2-thiophenecarboximidamide The experimental protocol used is the same as that described for compound 1.B.4, compound 13.6 replacing intermediate 1.B.3. A yellow solid product is obtained (yield 14%). Melting point: paste from 106° C.

Example 15 tert-butyl 3-{[amino(2-thienyl)methylidene]amino}benzyl{1-[5-(1,2-dithiolan-3-yl)pentanoyl]-4-piperidinyl}carbamate 15.1. N-(1-benzyl-4-piperidinyl)-N-(3-nitrobenzyl)amine 5.04 g (3.33 mmol) of 3-nitrobenzaldehyde and 7.48 ml (3.67 mmol) of 4-amino-1-benzylpiperidine are added successively, under an inert atmosphere, to a flask containing 100 ml of anhydrous methanol. The reaction mixture is stirred for 18 hours to produce the imine, then the addition is carried out, of 1.26 g (3.33 mmol) of $NaBH_4$ in portions. Stirring is maintained for another 24 hours before the addition of 5 ml of ice-cold water. The reaction mixture is then extracted twice with 100 ml of $CH_2Cl_2$. The organic phase is washed successively with 50 ml of water then 50 ml of salt water, dried over magnesium sulphate, filtered and concentrated under vacuum. The residue is purified on a silica column (eluent: dichloromethane containing 5% of ethanol). A yellow oil is obtained with a yield of 85%.

MH+=316.20.

15.2. tert-butyl 1-benzyl-4-piperidinyl(3-nitrobenzyl)carbamate

The experimental protocol used is the same as that described for compound 1.B.1, intermediate 15.1 replacing the 1-(4-nitrophenyl)piperazine. After treatment, a yellow oil is obtained which is sufficiently pure to be used in the following stage (yield 99%).

MH+=426.30.

15.3. tert-butyl 3-aminobenzyl(4-piperidinyl)carbamate

The experimental protocol used is the same as that described for compound 1.B.2, intermediate 15.2 replacing intermediate 1.B.1 and a dichloromethane/THF mixture (50/50) replacing the dichloromethane/ethanol mixture. A white-grey foam is obtained which is sufficiently pure to be used in the following stage (yield 63%).

MH+=306.30.

15.4. tert-butyl 3-{[amino(2-thienyl)methylidene]amino}benzyl(4-piperidinyl)carbamate The experimental protocol used is the same as that described for compound 1.B.3, intermediate 16.3 replacing intermediate 1.B.2 whilst two equivalents of dry pyridine are added to the reaction medium. After purification on a silica column (eluent: gradient ranging from pure dichloromethane to dichloromethane containing 10% of ethanol containing traces of ammonia), a yellowish-white foam is obtained, (yield 62%).

MH+=415.20.

15.5. tert-butyl 3-{[-amino(2-thienyl)methylidene]amino}benzyl{1-[5-(1,2-dithiolan-3-yl)pentanoyl]-4-piperidinyl}carbamate The experimental protocol used is similar to that described for compound 1.A.1, intermediate 16.4 replacing the nitrophenylpiperazine. The expected product is obtained in the form of a yellowish foam (yield 28%).

MH+=603.20.

Example 16

N'-{3-[({1-[5-(1,2-dithiolan-3-yl)pentanoyl]-4-piperidinyl}amino)methyl]phenyl}-2-thiophenecarboximidamide The experimental protocol used is the same as that described for compound 1.B.4, compound 15.5 replacing intermediate 1.B.3. A white solid is obtained (yield 33%)

MH+=503.31. .

Example 17

N-[2-(4-{[amino(2-thienyl)methylidene]amino}phenyl)ethyl]-4-{[5-(1,2-dithiolan-3-yl)pentanoyl]amino}benzamide 17.1. 4-[(tert-butoxycarbonyl)amino]benzoic acid The experimental protocol used is the same as that described for compound 1.B.1, with 4-aminobenzoic acid replacing the 1-(4-nitrophenyl)piperazine. A solid is obtained which is sufficiently pure to be used in the following stage (yield 23%).

MH+=238.

17.2. 3,5-dimethoxy-2-({[2-(4-nitrophenyl)ethyl]amino}methyl)phenol 9.0 g (49.4 mmol) of 4,6-dimethoxysalicaldehyde, 11.6 g (54.3 mmol) of 4-nitrophenethylamine hydrochloride and 7.5 ml of triethylamine are added successively into a flask containing 200 ml of anhydrous methanol, under an inert atmosphere. The reaction mixture is stirred vigorously for 15 hours before the addition, in portions, of 2.1 g (55.5 mmol) of $NaBH_4$. Stirring is maintained for an additional 10 hours before adding 10 ml of water. After quarter of an hour, the reaction mixture is extracted with twice 100 ml of $CH_2Cl_2$. The organic phase is washed successively with 50 ml of water and 50 ml of salt water, followed by drying over sodium sulphate, filtering and concentration under vacuum. The residue is then purified on a silica column (eluent: $CH_2Cl_2$/EtOH: 20/1). An orange oil is obtained with a yield of 58%.

17.3. tert-butyl 2-hydroxy-4,6-dimethoxybenzyl[2-(4-nitrophenyl)ethyl]carbamate 30.0 mmol of intermediate 17.2 is dissolved in a mixture of 100 ml of dichloromethane and 9.2 ml of triethylamine. The mixture is cooled down using an ice bath before the addition in several portions of 7.2 g (33.0 mmol) of $(Boc)_2O$. The reaction mixture is stirred at 23° C. for 12 hours and poured into a water-ice mixture. The organic phase is decanted, followed by washing successively with 20 ml of water and 20 ml of salt water. After drying over sodium sulphate, followed by filtration and concentration under vacuum, a white solid is obtained after trituration with isopropyl ether with a yield of 60%. Melting point: 133.5–134.4° C.

17.4. tert-butyl 2-(4-aminophenyl)ethyl(2-hydroxy-4,6-dimethoxybenzyl)carbamate:

A solution of intermediate 17.3 (20.2 mmol) in 66 ml of a dichloromethane, ethyl acetate and THF mixture (1 ml/60 ml/5 ml) as well as 1.0 g of 10% Pd/C is introduced into a stainless steel autoclave provided with a magnetic stirrer. The reaction mixture is stirred under hydrogen pressure (1.5 bars) for 12 hours at a temperature of 20° C. The Pd/C is then eliminated by filtration and the filtrate is concentrated under vacuum. A light yellow oil is obtained with a yield of 90%.

17.5. tert-butyl 2-(4-{[(amino(2-thienyl)methylidene]amino}phenyl)ethylcarbamate:

Intermediate 17.4 (2.37 mmol) is dissolved in 2-propanol (15 ml) and 1.014 g of S-methyl-2-thiophene thiocarboximide hydroiodide (3.56 mmol) (*Ann. Chim.* (1962), 7, 303–337) is added. After heating at 60° C. for 15 hours, the reaction mixture is concentrated to dryness under vacuum. The residue is taken up in dichloromethane and a saturated aqueous solution of $NaHCO_3$. After decantation, the organic phase is washed successively with 50 ml of a saturated solution of $NaHCO_3$, water and salt water. The organic solution is dried over magnesium sulphate, followed by filtration and evaporation under reduced pressure. The free base is then dissolved in 30 ml of dichloromethane and the solution is cooled down using an ice bath before the dropwise addition of 6.3 ml of a 1N HCl solution in anhydrous ethyl ether. After stirring for 15 hours at 25° C., the crystals obtained are filtered and rinsed in diethyl ether in order to obtain, after drying, a yellow solid with a yield of 79%. Melting point: 144° C.

17.6. N'-[4-(2-aminoethyl)phenyl]-2-thiophenecarboximidamide:

A stream of HCl gas is passed bubblewise at 0° C. through a solution of intermediate 17.5 (16.4 mmol) in a mixture (200 ml) of ether/ethanol/acetone/dichloromethane (1/1/1/1). The reaction medium is left to return to ambient temperature overnight. A stream of argon is passed through the reaction mixture and the solvents are evaporated to dryness. The evaporation residue is then poured into 100 ml of a cold saturated solution of $NaHCO_3$ and extracted with 3 times 100 ml of dichloromethane. The organic phase is dried over magnesium sulphate, followed by filtration and concentration under vacuum. Purification is then carried out on a silica column (eluent=heptane with 50% ethyl acetate then dichloromethane with 5% ethanol) in order to produce a white solid with a yield of 79%. Melting point: 169.2–170.5° C.

17.7. 4-amino-N-[2-(4-{[amino(2-thienyl)methylidene]amino}phenyl)ethyl]-benzamide The experimental protocol used is similar to that described for compound 1.A.1, intermediate 17.1 replacing the (DL)-thioctic acid and intermediate 17.6 replacing the nitrophenylpiperazine. The expected product is obtained in the form of a white foam with a yield of 35% (as well as a secondary product, tert-butyl 4-({[2-(4-{[amino(2-thienyl)methylidene]amino}phenyl)ethyl]amino}-carbonyl)phenylcarbamate, in the form of a white solid, with a yield of 14%).

MH+=365.20.

17.8. N-[2-(4-{[amino(2-thienyl)methylidene]amino}phenyl)ethyl]-4-{[5-(1,2-dithiolan-3-yl)pentanoyl]amino}benzamide The experimental protocol used is similar to that described for compound 1.A.1, intermediate 17.7 replacing the nitrophenylpiperazine. The expected product is obtained in the form of pale yellow crystals (yield 17%).

MH+=553.10.

Pharmacological Study of the Products of the Invention:
Study of the Effects on Neuronal Constitutive NO Synthase of a Rat's Cerebellum The inhibitory activity of the products of the invention is determined by measuring their effects on the conversion by NO synthase of [$^3$H]L-arginine to [$^3$H]L-citrulline according to the modified process of Bredt and Snyder (*Proc. Natl. Acad. Sci. USA,* (1990) 87: 682–685). The cerebellums of Sprague-Dawley rats (300 g-Charles River) are rapidly removed, dissected at 4° C. and homogenized in a volume of extraction buffer (HEPES 50 mM, EDTA 1 mM, pH 7.4, pepstatin A 10 mg/ml, leupeptin 10 mg/ml). The homogenates are then centrifuged at 21000 g for 15 min at 4° C. Dosage is carried out in glass test tubes in which 100 μl of incubation buffer containing 100 mM of HEPES (pH 7.4), 2 mM of EDTA, 2.5 mM of $CaCl_2$, 2 mM of dithiotreitol, 2 mM of reduced NADPH and 10 μg/ml of calmodulin are distributed. 25 μl of a solution containing 100 nM of [$^3$H]L-arginine (Specific activity: 56.4 Ci/mmole, Amersham) and 40 μM of non-radioactive L-arginine are added. The reaction is initiated by adding 50 μl of homogenate, the final volume being 200 μl (the missing 25 μl are either water or the tested product). After 15 minutes, the reaction is stopped with 2 ml of stopping buffer (20 mM of HEPES, pH 5.5, 2 mM of EDTA). After placing the samples through a 1 ml column of DOWEX resin, the radioactivity is quantified by a liquid scintillation spectrometer.

The compounds of Examples 1 to 6, 11, 12, 14 and 16 described above show an $IC_{50}$ lower than 4.5 μM.

Study of the Effects on the Oxidative Stress Induced by Glutamate on Cells in Culture (HT-22):

The inhibitory activity of the products of the invention is determined by measuring their ability to protect the cells of a mouse hippocampal cell line (HT-22) from oxidative stress caused by glutamate. The biosynthesis of glutathione, an essential element in cell detoxification of free radicals, requires the active transport of cystine to inside the cell. The glutamate by opposing the penetration of cystine causes a reduction in the level of gluthatione which leads to the death of the cell by oxidative stress (Demerle-Pallardy, C. et al., *J. Neurochem.* (2000), 74, 2079–2086; Davis, J. B. and Maher, P., *Brain Res.*, (1994) 652: 169–173; Murphy, T. H. et al., *Neuron,* (1989) 2: 1547–1558). The cells are cultured at 37° C. in a DMEM medium with 10% of fixtal calf serum added to it. The tests are carried out in 96-well plates containing 5000 cells per well. The glutamate (5 mM) is added to the medium containing or not containing the products to be tested. The cell viability is tested after 24 hours by the MTT process (Hansen, M. B. et al., *J Immunol.Processes* (1989) 119: 203–210). The ability of the compounds to protect the cells from the toxic action of the glutamate is estimated in $EC_{50}$, calculated relative to the viability of cells which have not been subjected to the action of the glutamate considered as 100% viability.

The compounds of Examples 1, 2, 4, 5 and 7 to 11 described above show an $EC_{50}$ lower or equal to 4 μM.

What is claimed is:
1. A compound of the formula

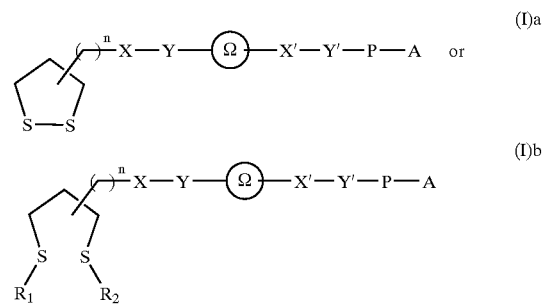

wherein n is an integer from 0 to 6;
$R_1$ and $R_2$ are individually selected from the group consisting of hydrogen and alkyl of 1 to 6 carbon atoms;
X-Y is selected from the group consisting of
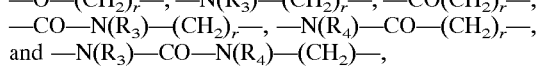
and —N(R$_3$)—CO—N(R$_4$)—(CH$_2$)—,
X'-Y' is selected from the group consisting of —(CH$_2$)$_r$—,
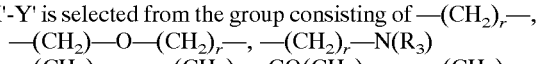
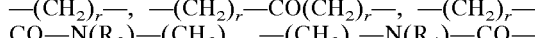
$R_3$ and $R_4$ are individually selected from the group consisting of hydrogen, alkyl, alkoxy-carbonyl and aralkoxycarbonyl;
r is independently each time that it occurs an integer from 0 to 6;

Ω is selected from the group consisting of aromatic heterocycle with 5 or 6 members, a non-aromatic heterocycle with 5 or 6 members, a non-aromatic heterocycle with 4 to 7 members and phenylene substituted by $R_5$, $R_5$ is selected from the group consisting of hydrogen, alkyl of 1 to 6 carbon atoms and —$(CH_2)_m$—;

Q is selected from the group consisting of halogen, hydroxyl, cyano, amino, alkoxy, alkylamino and dialkylamino, m is an integer from 0 to 6;

P is —$(CH_2)_g$—, g is an integer from 0 to 6, or P is

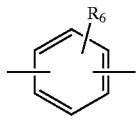

wherein $R_6$ is hydrogen, alkyl of 1 to 6 carbon atoms and —$(CH_2)_n$—Q',

Q' is halogen, trifluoromethyl, hydroxyl, amino, cyano, alkoxycarbonylamino, aralkoxycarbonylamino, alkoxy, alkylthio, alkylamino and dialkylamino, n is an integer from 0 to 6, or $R_6$ is aromatic or non-aromatic heterocycle with 5 to 6 ring members with the heteroatoms being selected from the group consisting of —O—, —N($R_7$)— and —S—, $R_7$ is hydrogen or alkyl of 1 to 6 carbon atoms;

and A is

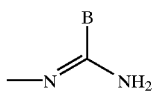

B is alkyl of 1 to 6 carbon atoms or carbocyclic or heterocyclic aryl with 5 or 6 ring members containing from 1 to 4 heteroatoms selected from the group consisting of O, S, N, the aryl being unsubstituted or substituted by at least one member selected from the group consisting of alkyl, alkenyl and alkoxy of up to 6 carbon atoms, or —B is —$NR_8R_9$, in which $R_8$ and $R_9$ are individually selected from the group consisting of hydrogen and alkyl of 1 to 6 carbon atoms, or one of $R_8$ and $R_9$ is nitro while the other is hydrogen or alkyl of 1 to 6 carbon atoms, or $R_8$ and $R_9$ taken together form with the nitrogen atom a non-aromatic heterocycle with five to six ring members, the elements of the chain being selected from the group consisting of —$CH_2$— —NH—, —O— and —S—, or B is $SR_{10}$, $R_{10}$ is hydrogen or alkyl of 1 to 6 carbon atoms;

or a pharmaceutically acceptable salt thereof.

2. A compound of claim 1 selected from the group consisting of

N'-(4-{4-[5-(1,2-dithiolan-3-yl)pentanoyl]-1-piperazinyl}phenyl)-2-thiophenecarboximidamide;

N'-(4-{4-[2-(1,2-dithiolan-3-yl)acetyl]-1-piperazinyl}phenyl)-2-thiophenecarboximidamide;

N'-[3-({4-[5-(1,2-dithiolan-3-yl)pentanoyl]-1-piperazinyl}methyl)phenyl]-2-thiophenecarboximidamide;

N'-[3-({4-[2-(1,2-dithiolan-3-yl)acetyl]-1-piperazinyl}methyl)phenyl]-2-thiophenecarboximidamide;

4-(4-{[amino(2-thienyl)methylidene]amino}phenyl)-N-[4-(1,2dithiolan-3-yl)butyl]-1-piperazinecarboxamide;

4-(4-{[amino(2-thienyl)methylidene]amino}-2-methylphenyl)-N-[4-(1,2-dithiolan-3-yl)butyl]-1-piperazinecarboxamide;

4-(4-{[amino(2-thienyl)methylidene]amino}-3-methylphenyl)-N-[4-(1,2-dithiolan-3-yl)butyl]-1-piperazinecarboxamide;

4-(4-{[amino(2-thienyl)methylidene]amino}-2-methoxyphenyl)-N-[4-(1,2-dithiolan-3-yl)butyl]-1-piperazinecarboxamide;

4-(4-{[amino(2-thienyl)methylidene]amino}-3-methoxyphenyl)-N-[4-(1,2-dithiolan-3-yl)butyl]-1-piperazinecarboxamide;

4-(4-{[amino(2-thienyl)methylidene]amino}-2-cyanophenyl)-N-[4-(1,2-dithiolan-3-yl)butyl]-1-piperazinecarboxamide;

4-(3-{[amino(2-thienyl)methylidene]amino}benzyl)-N-[4-(1,2-dithiolan-3-yl)butyl]-1-piperazinecarboxamide;

N'-(3-{4-[5-(1,2-dithiolan-3-yl)pentanoyl]-1-piperazinyl}phenyl)-2-thiophenecarboximidamide;

tert-butyl 5-{[amino(2-thienyl)methylidene]amino}-2-{4-[5-(1,2-dithiolan-3-yl)pentanoyl]-1-piperazinyl}benzylcarbamate;

N'-(3-(aminomethyl)-4-{4-[5-(1,2-dithiolan-3-yl)pentanoyl]-1-piperazinyl}phenyl)-2-thiophenecarboximidamide tert-butyl 3-{[-amino(2-thienyl)methylidene]amino}benzyl{1-[5-(1,2-dithiolan-3-yl)pentanoyl]-4-piperidinyl}carbamate;

N'-{3-[({1-[5-(1,2-dithiolan-3-yl)pentanoyl]-4-piperidinyl}amino)methyl]phenyl}-2-thiophenecarboximidamide; and N-[2-(4-{[amino(2-thienyl)methylidene]amino}phenyl)ethyl]-4-{[5-(1,2-dithiolan-3-yl)pentanoyl]amino}benzamide;

or a salt thereof.

3. A compound of claim 1 wherein B is selected from the group consisting of thiophene, furan, pyrrole and thiazole.

4. A compound of the formula (I) of claim 1 wherein B is thiophene; or a pharmaceutically acceptable salt of such a compound.

5. A compound of the formula (I) of claim 1 wherein P is

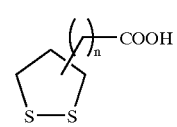

(Lvi)

and $R_6$ is selected from hydrogen, alkyl of 1 to 6 carbon atoms and —$(CH_2)_m$Q' wherein Q' is selected from halogen, trifluoromethyl, hydroxyl, amino, cyano and alkoxy of 1 to 6 carbon atoms and n is an integer from 0 to 6;

or a pharmaceutically acceptable salt of a salt of such a compound.

6. A process for the preparation of a compound of claim 1 in which the X—Y is —CO—N($R_3$)—$(CH_2)_r$—, comprising reacting a compound of the formula

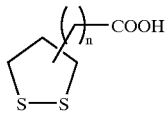
(Lvi)
wherein n has the meaning of claim 1 with an amine of the formula
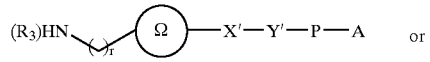
(X)
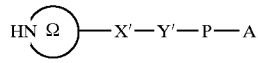
(Xa)
in which r, $R_3$, Ω, X', Y', P and A have the meaning of claim 1, the compound of formula (Xa) being such that its Ω heterocycle comprises a nitrogen atom.
\* \* \* \* \*